(12) United States Patent
Martin et al.

(10) Patent No.: US 12,153,043 B2
(45) Date of Patent: Nov. 26, 2024

(54) BI-SPECIFIC PROBES TO ENABLE THE USE OF SINGLE-CELL SAMPLES AS SINGLE COLOR COMPENSATION CONTROL

(71) Applicant: Becton, Dickinson and Company, Franklin Lakes, NJ (US)

(72) Inventors: Jody Martin, San Jose, CA (US); James Ghadiali, San Jose, CA (US); Mirko Corselli, San Jose, CA (US); Adam Wright, San Jose, CA (US); Aaron Jacob Tyznik, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 551 days.

(21) Appl. No.: 17/184,405

(22) Filed: Feb. 24, 2021

(65) Prior Publication Data

US 2021/0263019 A1     Aug. 26, 2021

Related U.S. Application Data

(60) Provisional application No. 63/021,363, filed on May 7, 2020, provisional application No. 62/981,479, filed on Feb. 25, 2020.

(51) Int. Cl.
G01N 33/53     (2006.01)

(52) U.S. Cl.
CPC ............... *G01N 33/5306* (2013.01)

(58) Field of Classification Search
CPC ....... G01N 15/1459; G01N 2015/1006; G01N 2015/1477; G01N 33/5306
See application file for complete search history.

(56) References Cited

U.S. PATENT DOCUMENTS

| | | | |
|---|---|---|---|
| 4,510,244 A | 4/1985 | Parks et al. | |
| 4,725,536 A | 2/1988 | Fritsch et al. | |
| 5,124,246 A | 6/1992 | Urdea et al. | |
| 5,137,809 A * | 8/1992 | Loken | G01N 15/1459 435/7.1 |
| 5,149,625 A | 9/1992 | Church et al. | |
| 5,200,314 A | 4/1993 | Urdea | |
| 5,308,990 A | 5/1994 | Takahashi et al. | |
| 5,424,186 A | 6/1995 | Fodor et al. | |
| 5,424,413 A | 6/1995 | Hogan et al. | |
| 5,445,934 A | 8/1995 | Fodor et al. | |
| 5,470,570 A * | 11/1995 | Taylor | C07K 16/28 424/153.1 |
| 5,604,097 A | 2/1997 | Brenner | |
| 5,635,352 A | 6/1997 | Urdea et al. | |
| 5,635,400 A | 6/1997 | Brenner | |
| 5,648,245 A | 7/1997 | Fire et al. | |
| 5,654,413 A | 8/1997 | Brenner | |
| 5,656,731 A | 8/1997 | Urdea | |
| 5,658,737 A | 8/1997 | Nelson et al. | |
| 5,714,330 A | 2/1998 | Brenner et al. | |
| 5,744,305 A | 4/1998 | Fodor et al. | |
| 5,759,778 A | 6/1998 | Li et al. | |
| 5,763,175 A | 6/1998 | Brenner | |
| 5,800,992 A | 9/1998 | Fodor et al. | |
| 5,830,712 A | 11/1998 | Rampersad et al. | |
| 5,846,719 A | 12/1998 | Brenner et al. | |
| 5,854,033 A | 12/1998 | Lizardi | |
| 5,871,928 A | 2/1999 | Fodor et al. | |
| 5,925,525 A | 7/1999 | Fodor et al. | |
| 5,935,793 A | 8/1999 | Wong | |
| 5,962,271 A | 10/1999 | Chenchik et al. | |
| 5,962,272 A | 10/1999 | Chenchik et al. | |
| 5,968,740 A | 10/1999 | Fodor et al. | |
| 5,981,176 A | 11/1999 | Wallace | |
| 5,981,179 A | 11/1999 | Lorinez et al. | |
| 6,013,445 A | 1/2000 | Albrecht et al. | |
| 6,040,138 A | 3/2000 | Lockhart et al. | |
| 6,046,005 A | 4/2000 | Ju et al. | |
| 6,060,596 A | 5/2000 | Lerner et al. | |
| 6,064,755 A | 5/2000 | Some | |

(Continued)

FOREIGN PATENT DOCUMENTS

| | | |
|---|---|---|
| CA | 2474509 A1 | 2/2003 |
| CA | 2961210 A1 | 3/2016 |

(Continued)

OTHER PUBLICATIONS

A printout retrieved from www.bdbiosciences.com/en-us/products/reagents/flow-cytometry-reagents/ research-reagents/compensation-beads on Sep. 21, 2023.*
Wang et al., "Development of Multicolor Flow Cytometry Calibration Standards: Assignment of Equivalent Reference Fluorophores (ERF) Unit," J. Res. Natl. Inst. Stand. Technol., 2011, vol. 116, No. 3, pp. 671-683.*
In re Couvaras, 2023 WL 3984753 (Fed. Cir. Jun. 14, 2023), pp. 1-11.*
10X Genomics, Inc., 2022, "Chromium Fixed RNA Profiling Reagent Kits," 10xGenomics.com, User Guide, in 95 pages.
Adey et al., "Rapid, low-input, low-bias construction of shotgun fragment libraries by high-density in vitro transposition," Genome Biology 2010, 11 (R19), in 17 pages.

(Continued)

*Primary Examiner* — Galina M. Yakovleva
(74) *Attorney, Agent, or Firm* — Dickinson Wright PLLC

(57) ABSTRACT

Disclosed herein include methods, compositions, and kits suitable for spectral unmixing and compensation in multi-parameter flow cytometry. Disclosed herein include reagents which comprise two antibodies conjugated to one another to form a bispecific reagent (e.g., a bispecific probe). A first antibody can have affinity for a highly expressed antigen on the surface of a cell of interest and a second antibody can have affinity for each of the antibody-dye conjugates in a multi-parameter panel. There are provided, in some embodiments, methods of using the bispecific reagent to determine spillover, perform compensation, and generate a compensation matrix.

23 Claims, 3 Drawing Sheets

(56) References Cited

U.S. PATENT DOCUMENTS

| | | |
|---|---|---|
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,309,306 B2 | 11/2012 | Nolan et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 8,865,470 B2 * | 10/2014 | Yan ............... G01N 21/6486 |
| | | 436/171 |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,567,645 B2 | 2/2017 | Fan et al. |
| 9,567,646 B2 | 2/2017 | Fan et al. |
| 9,582,877 B2 | 2/2017 | Fu et al. |
| 9,593,365 B2 | 3/2017 | Frisen et al. |
| 9,598,736 B2 | 3/2017 | Fan et al. |
| 9,637,799 B2 | 5/2017 | Fan et al. |
| 9,644,204 B2 | 5/2017 | Hindson et al. |
| 9,677,131 B2 | 6/2017 | Fredriksson et al. |
| 9,689,024 B2 | 6/2017 | Hindson et al. |
| 9,695,468 B2 | 7/2017 | Hindson et al. |
| 9,727,810 B2 | 8/2017 | Fodor et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,208,356 B1 | 2/2019 | Fan et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,253,375 B2 | 4/2019 | Fan et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |

(56) References Cited

U.S. PATENT DOCUMENTS

| | | |
|---|---|---|
| 10,338,066 B2 | 7/2019 | Fan et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 10,676,779 B2 | 6/2020 | Chang et al. |
| 10,869,570 B2 | 6/2020 | Chang et al. |
| 10,927,419 B2 | 2/2021 | Fan et al. |
| 10,941,396 B2 | 3/2021 | Fu et al. |
| 10,954,570 B2 | 3/2021 | Fan et al. |
| 11,092,607 B2 | 8/2021 | Gaublomme et al. |
| 11,390,914 B2 | 7/2022 | Fu et al. |
| 11,460,468 B2 | 10/2022 | Fan et al. |
| 11,467,157 B2 | 10/2022 | Fan et al. |
| 11,535,882 B2 | 12/2022 | Fu et al. |
| 11,634,708 B2 | 4/2023 | Fu et al. |
| 11,661,625 B2 | 5/2023 | Jensen et al. |
| 11,773,441 B2 | 10/2023 | Fan et al. |
| 11,782,059 B2 | 10/2023 | Fan et al. |
| 11,932,849 B2 | 3/2024 | Shum |
| 11,932,901 B2 | 3/2024 | Song et al. |
| 11,939,622 B2 | 3/2024 | Song |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0208936 A1 | 8/2009 | Tan et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2011/0319289 A1 | 12/2011 | Libutti |
| 2012/0004132 A1 | 1/2012 | Zhang et al. |
| 2012/0010091 A1 | 1/2012 | Linnarson |

(56) References Cited

U.S. PATENT DOCUMENTS

| | | |
|---|---|---|
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0080266 A1 | 3/2015 | Volkmuth et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0148685 A1 | 5/2015 | Baym |
| 2015/0152409 A1 | 6/2015 | Seitz et al. |
| 2015/0203897 A1 | 7/2015 | Robons et al. |
| 2015/0211050 A1 | 7/2015 | Lafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2016/0362730 A1 | 12/2016 | Alexander et al. |
| 2017/0044525 A1 | 2/2017 | Kaper et al. |
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0016634 A1 | 1/2018 | Hindson et al. |
| 2018/0024139 A1 | 1/2018 | Peikon et al. |
| 2018/0030504 A1 | 2/2018 | Nolan et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |

(56) References Cited

U.S. PATENT DOCUMENTS

| | | |
|---|---|---|
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0245069 A1 | 8/2018 | Desantis et al. |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340169 A1 | 11/2018 | Belhocine et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0145982 A1 | 5/2019 | Chee et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |
| 2023/0083422 A1 | 3/2023 | Fu et al. |
| 2023/0109336 A1 | 4/2023 | Shum et al. |
| 2023/0125113 A1 | 4/2023 | Fan et al. |
| 2023/0193372 A1 | 6/2023 | Shum et al. |

FOREIGN PATENT DOCUMENTS

| | | |
|---|---|---|
| CN | 106460033 A | 2/2017 |
| CN | 107208158 A | 9/2017 |
| CN | 110498858 A | 11/2019 |
| DE | 102008025656 | 12/2009 |
| EP | 1473080 A2 | 11/2004 |
| EP | 1647600 A2 | 4/2006 |
| EP | 1845160 A1 | 10/2007 |
| EP | 2036989 A1 | 3/2009 |
| EP | 1379693 B1 | 5/2009 |
| EP | 2204456 A1 | 7/2010 |
| EP | 2431465 A1 | 3/2012 |
| EP | 2203749 B1 | 8/2012 |
| EP | 2511708 A1 | 10/2012 |
| EP | 2538220 A1 | 12/2012 |
| EP | 2623613 A1 | 8/2013 |
| EP | 1745155 B1 | 10/2014 |
| EP | 2805769 A1 | 11/2014 |
| EP | 2556171 B1 | 9/2015 |
| EP | 2970958 B1 | 12/2017 |
| EP | 3263715 A1 | 1/2018 |
| EP | 2670863 B1 | 6/2018 |
| EP | 3136103 B1 | 8/2018 |
| EP | 2954102 B1 | 12/2018 |
| EP | 3428290 A1 | 1/2019 |
| EP | 2970957 B1 | 4/2019 |
| EP | 3058092 B1 | 5/2019 |
| EP | 3256606 B1 | 5/2019 |
| EP | 3327123 B1 | 8/2019 |
| EP | 3587589 A1 | 1/2020 |
| GB | 2293238 A | 3/1996 |
| JP | H04108385 | 4/1992 |
| JP | 2001078768 A | 3/2001 |
| JP | 2005233974 A | 9/2005 |
| JP | 2007504831 A | 3/2007 |
| JP | 2008256428 A | 10/2008 |
| JP | 2013039275 A | 2/2013 |
| JP | 2018509896 A | 4/2018 |
| JP | 2018535652 A | 12/2018 |
| JP | 2019522268 | 8/2019 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001020035 | 3/2001 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |

(56) References Cited

FOREIGN PATENT DOCUMENTS

| | | |
|---|---|---|
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010048605 | 4/2010 |
| WO | WO2010059820 | 5/2010 |
| WO | WO2010117620 | 10/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012106385 | 8/2012 |
| WO | WO2012106546 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013137737 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014062717 | 4/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2018015365 | 1/2015 |
| WO | WO2015017586 | 2/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015188839 | 12/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016176091 | 11/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018018008 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |

(56) References Cited

FOREIGN PATENT DOCUMENTS

| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018152129 | 8/2018 |
| WO | WO2018165366 | 9/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167830 | 8/2020 |
| WO | WO2020167920 | 8/2020 |
| WO | WO2020214642 | 10/2020 |
| WO | WO2020219721 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO2021178199 | 9/2021 |
| WO | WO2021231779 | 11/2021 |
| WO | WO2021247593 | 12/2021 |
| WO | WO2021257795 | 12/2021 |
| WO | WO2022015667 | 1/2022 |
| WO | WO2022026909 | 2/2022 |
| WO | WO2022040453 | 2/2022 |
| WO | WO2022115608 A1 | 2/2022 |
| WO | WO2022115608 A9 | 2/2022 |
| WO | WO2022076912 | 4/2022 |
| WO | WO2022109339 | 5/2022 |
| WO | WO2022109343 | 5/2022 |
| WO | WO2022132206 | 6/2022 |
| WO | WO2022143221 | 7/2022 |
| WO | WO2022256324 | 12/2022 |
| WO | WO2023034739 | 3/2023 |
| WO | WO2023034789 | 3/2023 |
| WO | WO2023034790 | 3/2023 |
| WO | WO2023034794 | 3/2023 |
| WO | WO2023034872 | 3/2023 |
| WO | WO2023039433 | 3/2023 |

OTHER PUBLICATIONS

Advisory Action dated May 31, 2023 in U.S. Appl. No. 16/789,311.

Ahern, "Biochemical, Reagent Kits Offer Scientists Good Return on Investment," The Scientist 1995, 9(15), in 5 pages.

Arguel et al., "A cost effective 5' selective single cell transcriptome profiling approach with improved UMI design," Nucleic Acids Research 2017, 45(7), e48, in 11 pages.

Bolivar et al., "Targeted next-generation sequencing of endometrial cancer and matched circulating tumor DNA: identification of plasma-based, tumor-associated mutations in early stage patients," Modern Pathology 2019, 32(3), 405-414.

Brouilette et al., "A Simple and Novel Method for RNA-seq Library Preparation of Single Cell cDNA Analysis by Hyperactive Tn5 Transposase," Developmental Dynamics 2012, 241, 1584-1590.

Buenrostro et al., "Transposition of native chromatin for multimodal regulatory analysis and personal epigenomics," Nat Methods 2013, 10(12), 1213-1218.

Buenrostro et al., "ATAC-seq: A Method for Assaying Chromatin Accessibility Genome-Wide," Curr Protoc Mol Biol 2016, 109, 1-21.

Chang et al., "Single-cell protein and gene expression profiling of stem memory T cells by BD Ab-seq," Annual Joint Meeting of the American Society for Cell Biology and the European Molecular Biology Organization 2017, 28(26), p. 1896.

Chen et al., "High-throughput sequencing of the transcriptome and chromatin accessibility in the same cell," Nature Biotechnology 2019, 37, 1452-1457.

De Simone et al., "Single Cell T Cell Receptor Sequencing: Techniques and Future Challenges," Frontiers in Immunology 2018, 9(1638), 1-7.

Delebecque, C. J., Silver, P.A., & Lindner, A. B. Designing and using RNA scaffolds to assemble proteins in vivo. Nature protocols, 2012, 7(10), 1797-1807.

Dengl et al., "Engineered hapten-binding antibody derivatives for modulation of pharmacokinetic properties of small molecules and targeted payload delivery," Immunol Rev. 2016, 270, 165-177.

Dickey and Giangrande. "Oligonucleotide Aptamers: A Next-Generation Technology for the Capture and Detection of Circulating Tumor Cells." Methods 97 2016: 94-103.

Dovgan et al., "Antibody—Oligonucleotide Conjugates as Therapeutic, Imaging, and Detection Agents," Bioconjugate Chem. 2019, 30, 2483-2501.

Dua, et al. Patents on SELEX and therapeutic aptamers. Recent patents on DNA & gene sequences, 2008, 2( 3), 172-186.

Erickson et al., "AbSeq Protocol Using the Nano-Well Cartridge-Based Rhapsody Platform to Generate Protein and Transcript Expression Data on the Single-Cell Level," STAR Protocols 2020, in 31 pages.

Eulberg, D., Buchner, K., Maasch, C., & Klussmann, S. . Development of an automated in vitro selection protocol to obtain RNA-based aptamers: identification of a biostable substance P antagonist. Nucleic acids research, 2005, 33(4), e45. https://doi.org/10.1093/nar/gni044.

Examination Report dated Oct. 8, 2021 in European Patent Application No. 18716877.8.

Examination Report dated Nov. 18, 2021 in European Patent Application No. 19724003.9.

Examination Report dated Nov. 24, 2021 in European Patent Application No. 19762517.1.

Examination Report dated Dec. 6, 2021 in European Patent Application No. 18703156.2.

Examination Report dated Dec. 9, 2021 in European Patent Application No. 19723988.2.

Examination Report dated Apr. 7, 2022 in Singapore Patent Application No. 10201806890V.

Examination Report dated Apr. 8, 2022 in Australian Patent Application No. 2018281745.

Fathi,, P. Design and Characterization of SSDNA Aptamer Candidates to Bind Bacteroides Fragilis Toxin Subtypes BFT-1 and BFT-2 (Doctoral dissertation, Johns Hopkins University).2017.

Final Office Action dated Jun. 15, 2021 in U.S. Appl. No. 15/084,307.

Final Office Action dated Jul. 15, 2021 in U.S. Appl. No. 16/836,750.

Final Office Action dated Aug. 10, 2021 in U.S. Appl. No. 16/012,584.

(56) References Cited

OTHER PUBLICATIONS

Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
Final Office Action dated Apr. 25, 2023 in U.S. Appl. No. 16/525,054.
Final Office Action dated May 15, 2023 in U.S. Appl. No. 16/551,638.
Final Office Action dated May 19, 2023 in U.S. Appl. No. 17/163,177.
Final Office Action dated May 31, 2023 in U.S. Appl. No. 16/934,530.
Final Office Action dated Jun. 8, 2023 in U.S. Appl. No. 17/147,283.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
Hoinka, Jan, and Teresa Przytycka. "AptaPLEX-A Dedicated, Multithreaded Demultiplexer for HT-SE LEX Data." Methods, 2016, 106 82-85.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Ku, Ti-Hsuan et al. "Nucleic Acid Aptamers: An Emerging Tool for Biotechnology and Biomedical Sensing." Sensors, 2015, 15. 7: 16281-16313.
Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Lee et al., "Comparison of Surface Markers between Human and Rabbit Mesenchymal Stem Cells," PLoS ONE 2014, 9(11), in 10 pages.
Livingstone, "rRNA depletion, poly(A) enrichment, or exonuclease treatment?" Tebu-Bio Blog 2015, in 1 page.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Mairal, Teresa et al. "Aptamers: Molecular Tools for Analytical Applications." Analytical and bioanalytical chemistry 2008,390.4: 989-1007.
Mayer et al., "Obtaining deeper insights into microbiome diversity using a simple method to block host and nontargets in amplicon sequencing," Molecular Ecology Resources 2021, 21(6), 1952-1965.
Minnoye et al., "Chromatin accessibility profiling methods," Nature Reviews Method Primers 2021, 1-24.
Monneron, "One-step Isolation and Characterization of Nuclear Membranes, 1974 Electron Microscopy and Composition of Biological Membranes and Envelops," The Royal Publishing Society 1974, 268, 101-108.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.

(56) References Cited

OTHER PUBLICATIONS

Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 3, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Non-Final Office Action dated Apr. 26, 2023 in U.S. Appl. No. 16/540,971.
Non-Final Office Action dated Apr. 26, 2023 in U.S. Appl. No. 16/374,626.
Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean Patent Application No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 26, 2022 in Chinese Patent Application No. 201780058799.1.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Notice of Allowance dated Jun. 8, 2023 in U.S. Appl. No. 16/459,444.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794 .
Office Action dated Sep. 14, 2021, in Chinese Patent Application No. 2016800523302.
Office Action dated Oct. 21, 2021, in Chinese Patent Application No. 2016800073512.

(56) References Cited

OTHER PUBLICATIONS

Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 2017800587991.
Office Action dated Feb. 9, 2022 in Japanese Patent Application No. 2019-540515.
Office Action dated Mar. 7, 2022 in Korean Patent Application No. 10-2022-7004715.
Office Action dated May 2, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.
Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Nov. 24, 2022 in Chinese Patent Application No. 2018800147939.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Office Action dated Apr. 24, 2023 in European Patent Application No. 21714995.4.
Office Action dated Apr. 26, 2023 in European Patent Application No. 18703156.2.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated Jun. 1, 2023 in Japanese Patent Application No. 2020-561807.
Office Action dated Jun. 16, 2023 in Chinese Patent Application No. 2019800708938.
Office Action dated Jun. 22, 2023 in Japanese Patent Application No. 2022-071002.
Office Action dated Jul. 12, 2023 in Chinese Patent Application No. 2020800212600.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 3, 2023 in U.S. Appl. No. 17/161,558.
Restriction Requirement dated Jun. 28, 2023 in U.S. Appl. No. 17/336,055.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Takara Bio, "SMARTer Human BCR IgG IgM H/K/L Profiling Kit User Manual," Takara Bio USA Inc. 2019, 1-22.
Trzupek et al., "Discovery of CD8O and CD86 as recent activation markers on regulatory T cells by protein-RNA single-cell analysis", Genome Medicine 2020, 12(1), in 22 pages.
Uellendahl-Werth et al., "A benchmark of hemoglobin blocking during library preparation for mRNA Sequencing of human blood samples," Scientific Reports 2020, 10(1), 5630.
Wang et al., "Tagmentation-based whole-genome bisulfite sequencing," Nature Protocols 2013, 8(10), 2022-2032.
Wangsanuwat et al., "Efficient and cost-effective bacterial mRNA sequencing from low input samples through ribosomal RNA depletion," BMC Genomics 2020, 21(1), 1-12.
WU & Lambowitz, "Facile single-stranded DNA sequencing of human plasma DNA via thermostable group II intron reverse transcriptase template switching," Scientific Reports 2017, 7(8421), 1-14.
Yang & Zhao, "Quantitative Analysis of Nonoxynol-9 in Blood," Contraception 1991, 43(2), 161-166.
Zhang et al., "Immunoaffinity Purification of Plasma Membrane with Secondary Antibody Superparamagnetic Beads," Journal of Proteome 2006, 6, 34-43.

(56) References Cited

OTHER PUBLICATIONS

Zheng, Fuyin et al. "Aptamer-Functionalized Barcode Particles for the Capture and Detection of Multiple Types of Circulating Tumor Cells." Advanced materials (Weinheim), 2014, 26.43: 7333-7338.
Zhou, Jiehua, and John Rossi. "Aptamers as Targeted Therapeutics: Current Potential and Challenges." Nature reviews. Drug discovery, 2017, 16.3: 181-202.
Zhulidov et al., "Simple cDNA normalization using kamchatka crab duplex-specific nuclease," Nucleic Acids Research. 2004, 32(3)e37.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLID™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, Aug. 21, 2010, "Useful fundamental numbers in molecular biology," http://bionumbers.hms.harvard.edu/KeyNumbers/aspx, 1-4.
Biosciences Product Catalogue, Dynal® Catalog 1999, Oslo, Norway, 49-51.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis, " Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.

(56) References Cited

OTHER PUBLICATIONS

Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "Smart™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Complaint filed in Becton, *Dickinson and Company and Cellular Research Inc.* v. *10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.

(56) References Cited

OTHER PUBLICATIONS

Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Extended European Search Report dated May 6, 2021 in European Patent Application No. 20207621.2.
Extended European Search Report dated May 28, 2021 in European Patent Application No. 20209777.0.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Fitzgerald and Grivel, "A Universal Nanoparticle Cell Secretion Capture Assay," Cytometry Part A 2012, 83A(2), 205-211.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.

(56) References Cited

OTHER PUBLICATIONS

Fu et al., "Molecular indexing enables quantitative targeted RNA sequencing and reveals poor efficiencies in standard library preparation," PNAS 2014, 111(5), 1891-1896.
GenBank Accession No. NM_000518.5 for *Homo sapiens* hemoglobin subunit beta (HBB), mRNA. Mar. 22, 2021 [online], [retrieved on Apr. 27, 2021], retrieved from the Internet: <URL: www.ncbi.nlm.nih.gov/nuccore/NM_000518.5?report=Genbank (Year: 2021).
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Grounds for Opposition dated Jul. 21, 2016 and filed in European Patent 2414548B1.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Aug. 6, 2019 in PCT Application No. PCT/US2018/014385.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Preliminary Report on Patentability dated Feb. 9, 2021 in PCT Application No. PCT/US2019/043949.
International Preliminary Report on Patentability dated Feb. 23, 2021 in PCT Application No. PCT/US2019/046549.
International Preliminary Report on Patentability dated Mar. 2, 2021 in PCT Application No. PCT/US2019/048179.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.

(56) References Cited

OTHER PUBLICATIONS

International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in in PCT Application No. PCT/US2021/013109.
International Search Report and Written Opinion dated May 11, 2021 in PCT Application No. PCT/US2021/013748.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute Nos. of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.
Kotake et al., "A simple nested RT-PCR method for quantitation of the relative amounts of multiple cytokine mRNAs in small tissue samples," Journal of Immunological Methods 1996, 199, 193-203.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.

(56) References Cited

OTHER PUBLICATIONS

Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., Universal process-inert encoding architecture for polymer2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," ThermoFisher Scientific, Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in Bacillus subtilis," Science 2007, 317, 526-529.
Macaulay et al., "Single Cell Genomics: Advances and Future Perspectives," PLoS Genetics 2014, 10(1), 1-9.
Macaulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., "Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
New COVID-19 Variants, Centers for Disease Control and Prevention 2021, accessed Jan. 21, 2021, 3 pp.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.

(56) References Cited

OTHER PUBLICATIONS

Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Sep. 23, 2020 in Korean Patent Application No. 10-2016-7008144.
Notice of Allowance dated Oct. 29, 2020 in U.S. Appl. No. 15/987,851.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.

(56) References Cited

OTHER PUBLICATIONS

Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1 .
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787 .
Office Action dated May 21, 2021 in Chinese Patent Application No. 201680007351.2.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and—Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes andsample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for

(56) References Cited

OTHER PUBLICATIONS high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tagsfrom a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody—DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.KO, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stoeckius et al., "Cell Hashing with barcoded antibodies enables multiplexing and doublet detection for single cell genomics," Genome Biology 2018, 19(224), 1-12.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.

(56) References Cited

OTHER PUBLICATIONS

Summons to Attend Oral Proceedings dated Nov. 16, 2020 in European Patent Application No. 17202409.3.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for mycobacterium tuberculosis DNA," Journal of Clinical Microbiology 2006, 44, 1029-1039.
Tan et al., "Genome-wide comparison of DNA hydroxymethylation in mouse embryonic stem cells andneural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
TotalSeq™-A0251 anti-human Hashtag 1 Antibody, BioLegend®, Jul. 2018, 1-10.
Treutlein et al., "Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vestheim et al., "Application of Blocking Oligonucleotides to Improve Signal-to-Noise Ratio in a PCR," Methods in Molecular Biology 2011, 687, 265-274.
Vogelstein et al., "Digital PCR," Proc. Natl. Acad. Sci. 1999, 96, 9236-9241.
Vollbrecht et al., "Validation and comparison of two NGS assays for the detection of Egfr T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," Bio Techniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., "Fluorescent microsphere-based readout technology for multiplexed human single nucleotide polymorphism analysis and bacterial identification," Human Mutation 2001, 17(4), 305-316.
Yoon et al., "Sensitive and accurate detection of copy number variants using read depth of coverage," Genome Res. 2009, 19, 1586-1592.
Zeberg et al., "The major genetic risk factor for severe COVID-19 is inherited from Neanderthals," Nature 2020, 587(7835), 1-13.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A Smart Approach for Full-Length cDNA Library Construction," BioTechniques 2001, 30(4), 892-897.
Armbrecht, et al. "Single-cell protein profiling in microchambers with barcoded beads", Microsystems & Nanoengineering, 2019, 5:55.
Decision of Grant dated Aug. 21, 2023 in Japanese Patent Application 2020-561800.
Examination Report dated Oct. 31, 2023 in European Patent Application 20753616.0.
Examination Report dated Nov. 9, 2023 in European Patent Application 20711394.5.
Extended European Search Report Dated Oct. 4, 2023 in European Patent Application No. 23166582.9.
Final Office Action dated Oct. 5, 2023 in U.S. Appl. No. 17/151,050.
Final Office Action dated Oct. 13, 2023 in U.S. Appl. No. 15/055,407.
Final Office Action dated Oct. 23, 2023 in U.S. Appl. No. 16/540,971.
Illumina, "Data Processing of Nextera Mate Pair Reads on Illumina Sequencing Platforms", Data Processing Technical Note from 2012.

(56) References Cited

OTHER PUBLICATIONS

International Search Report and Written Opinion dated Jun. 5, 2023, in PCT Application No. PCT/US2023/061980.
International Search Report and Written Opinion dated Jun. 23, 2023 in PCT Application No. PCT/US2023/062070.
Invitrogen, "The attraction is simply magnetisk, Dynabeads® Streptavidin products and applications" Invitrogen, 2010, 1-8.
Ko, "An 'equalized cDNA library' by the reassociation of short double-stranded cDNAs," Nucleic Acids Res. 1990, 18(19), 5705-5711.
Livingstone, "rRNA depletion, poly(A) enrichment, or exonuclease treatment?" Tebu-Bio Blog 2015,. 5 pgs.
Non-Final Office Action dated Jun. 30, 2023 In U.S. Appl. No. 17/684,289.
Non-Final Office Action dated Jul. 27, 2023 in U.S. Appl. No. 17/373,519.
Non-Final Office Action dated Sep. 21, 2023 in Canadian Patent Application No. 3,034,924.
Non-Final Office Action dated Sep. 28, 2023 in U.S. Appl. No. 16/789,311.
Non-Final Office Action Dated Sep. 28, 2023 in U.S. Appl. No. 17/184,405.
Non-Final Office Action Dated Oct. 5, 2023 in U.S. Appl. No. 16/848,241.
Non-Final Office Action Dated Nov. 7, 2023 in U.S. Appl. No. 17/528,104.
Notice of Allowance dated Aug. 23, 2023 in Canadian Patent Application No. 2,865,575.
Notice of Allowance dated Aug. 25, 2023 in European Patent Application No. 22 200 785.8.
Notice of Allowance dated Aug. 28, 2023 in U.S. Appl. No. 16/374,626.
Notice of Allowance dated Sep. 14, 2023 in Canada Application No. 2982467.
Notice of Allowance dated Sep. 29, 2023 in European Application No. 22165594.7.
Notice of Allowance dated Oct. 2, 2023 in European Application 21735067.8.
Notice of Allowance dated Oct. 25, 2023 in European Application 20816802.1.
Office Action dated May 30, 2023 in Chinese Patent Application No. 2019800653102.
Office Action dated Jun. 28, 2023 in European Patent Application 19836239.4.
Office Action dated Jul. 12, 2023 in Canadian Patent Application No. 3,059,559.
Office Action Dated Jul. 13, 2023 in Chinese Patent Application No. 202080077712.7.
Office Action dated Jul. 28, 2023 in Chinese Patent Application No. 201880014793.9.
Office Action dated Jul. 29, 2023 in Chinese Patent Application No. 201980073850.5.
Office Action dated Jul. 31, 2023 in Chinese Patent Application No. 201980068704.3.
Office Action dated Jul. 31, 2023 in Chinese Patent Application No. 201980037175.0.
Office Action dated Aug. 11, 2023 in European Patent Application 19752792.2.
Office Action dated Aug. 21, 2023 in Japanese Patent Application No. 2021-507836.
Office Action dated Aug. 30, 2023 in Chinese Patent Application 2019111653930.
Office Action dated Aug. 31, 2023 in Chinese Patent Application 2020800483617.
Office Action dated Sep. 21, 2023 in Japanese Patent Application 2022-030956.
Office Action dated Sep. 21, 2023 in Israel Patent Application 265478.
Office Action dated Oct. 10, 2023 in European Patent Application 16719706.0.
Office Action dated Oct. 13, 2023 in Chinese Patent Application 202080014409.2.
Office Action dated Oct. 19, 2023 in Japanese Patent Application 2019-566787.
Office Action dated Oct. 23, 2023 in Japanese Patent Application 2021-517856.
Office Action dated Oct. 26, 2023 In Japanese Patent Application 2022-525692.
Office Action Dated Oct. 30, 2023 in Japanese Patent Application 2021-523956.
Office Action Dated Nov. 9, 2023 in Japanese Patent Application 2017-549390.
Ogawa, T. et al., "The Efficacy and further functional advantages of random-base molecular barcodes for absolute and digital quantification of nucleic acid molecules", Sci Rep 7, 2017 12576.
Restriction Requirement dated Oct. 5, 2023 in U.S. Appl. No. 17/373,653.
Restriction Requirement dated Oct. 11, 2023 in U.S. Appl. No. 17/531,555.
Summons to Attend Oral Proceedings Dated Aug. 8, 2023 in European Patent Application No. 14749671.5.
10x_LIT099_Product-Sheet_Chromium-Single-Cell-Multiome-ATAC-Gene-Expression_Letter_digital_2021.
AAT Bioquest, Calcein-Based Cell Viability Assays, AssayWise Letters, 2016, 5(1), 1-16.
Blumenthal, "RNA Replication: Function and Structure of Qb-Replicase" Ann. Rev. Biochem. 1979. 48:525-48.
Cahill et al., "Polymerase Chain Reaction and Qb Replicase Amplification" Clin. Chem. 1991, 37(9) 1482-1485.
CG000209_Chromium_NextGEM_SingleCell_ATAC_ReagentKits_v1.1_UserGuide_RevG_2022.
CG000496_Chromium_NextGEM_SingleCell_ATAC_ReagentKits_v2_UserGuide_RevB 2022.
CG000505_Chromium_Nuclei_Isolation_Kit_UG_RevA_2022.
Chen et al., "Single-Cell Protein Secretion Detection and Profiling", Annual Reviews, Anal. Chem, 2019, 12, 431-449.
Corrected Notice of Allowability dated Aug. 25, 2023 in U.S. Appl. No. 16/459,444.
Corrected Notice of Allowability dated Mar. 27, 2024 in U.S. Appl. No. 17/370,923.
Decision to Grant dated Oct. 18, 2018 in European Patent Application No. 1461937.3.
Decision to Grant dated Oct. 14, 2021 in European Patent Application No. 17202409.3.
Decision to Grant dated Jul. 20, 2023 in European Patent Application No. 17781265.8.
Decision to Grant dated Feb. 29, 2024 in European Patent Application No. 21735076.8.
Decision to Grant Dated Jul. 8, 2024 in Japanese Patent Application 2019-566787.
Decision of Grant dated Nov. 27, 2023 In Japanese Patent Application No. 2021-505735.
Decision of Grant dated Dec. 4, 2023 in Japanese Patent Application No. 2022-096387.
Dey et al., "Integrated genome and transcriptome sequencing of the same cell", Nature Biotechnology, 33(3) 2015, 285.
Examination Report dated May 17, 2022 in Australian Patent Application No. 2019204928.
Examination Report dated Apr. 18, 2024 in Australian Patent Application No. 2022211826.
Examination Report dated Sep. 21, 2023 in Canadian Patent Application No. 3,034,924.
Examination Report dated Oct. 25, 2021 in European Patent Application No. 17781265.8.
Examination Report dated Nov. 24, 2023 in European Patent Application No. 20209777.0.
Examination Report dated Mar. 6, 2024 in European Patent Application No. 19836239.4.
Examination Report dated Apr. 19, 2024 in European Patent Application No. 23166391.5.
Examination Report dated Mar. 18, 2019 in Singapore Patent Application No. 11201405274W.

(56) References Cited

OTHER PUBLICATIONS

Extended European Search Report dated Feb. 23, 2024 in European Patent Application No. 23191518.2.
Extended European Search Report dated Jun. 3, 2024 in European Application 23216012.7.
Final Office Action dated Dec. 27, 2023 in U.S. Appl. No. 17/174,249.
Final Office Action dated Feb. 9, 2024 in U.S. Appl. No. 17/151,058.
Final Office Action dated Mar. 21, 2024 in U.S. Appl. No. 16/788,743.
Final Office Action dated Apr. 9, 2024 in U.S. Appl. No. 17/147,283.
Final Office Action dated May 8, 2024 in U.S. Appl. No. 17/373,653.
Final Office Action dated May 13, 2024 in U.S. Appl. No. 17/157,872.
Final Office Action dated May 30, 2024 in U.S. Appl. No. 17/528,104.
Final Office Action dated Jun. 18, 2024 in U.S. Appl. No. 16/551,620.
Fisher Scientific, Invitrogen Calcein AM, Cell-Permanent Green and Blue Dyes, Invitrogen, 2024, 1-4.
Gerlach, et al., "Combined quantification of intracellular (phospho-) proteins and transcriptomics from fixed single cells", Scientific Reports, 2019 vol. 9:1469, pp. 1-10.
Human Genome, Wikipedia.com, accessed Aug. 4, 2021.
Illumina, "Estimating Sequencing Coverage" Technical Note: Sequencing from 2014.
Illumina, "Optimizing Cluster Density on Illumina Sequencing Systems", Publication No. 770-2014-031, 2016.
International Preliminary Report on Patentability dated Mar. 26, 2019 in PCT Application No. PCT/US2017/053331.
International Search Report and Written Opinion dated Jan. 12, 2024 in PCT Application No. PCT/US2023/078302.
International Search Report and Written Opinion dated Feb. 27, 2024 in PCT Application No. PCT/US2023/036545.
International Search Report and Written Opinion dated Jun. 11, 2024 in PCT Application No. PCT/US2023/084669.
Lebl et al. "A High-Complexity, Multiplexed Solution-Phase Assay for Profiling Protease Activity oin Microarrays", Combinatorial Chemistry and High Throughput Screening, 2008, 11(1), 24-35.
Lustig et al., J of Molecular Biology 180 :753-759 1984.
Murinae, Wikipedia.com, pp. 1-12, accessed Jun. 10, 2024.
Nair, et al., "Enzymatic cleavage of uracil-containing single-stranded DNA linkers for the efficient release of affinity-selected circulating tumor cells" Chem Commun (Camb). Feb. 21, 2015 ;51 (15):3266- 9.
Non-Final Office Action dated Dec. 28, 2023 in U.S. Appl. No. 17/157,872.
Non-Final Office Action dated Jan. 2, 2024 in U.S. Appl. No. 17/373,653.
Non-Final Office Action dated Jan. 19, 2024 in U.S. Appl. No. 17/336,055.
Non-Final Office Action dated Feb. 9, 2024 in U.S. Appl. No. 16/846,133.
Non-Final Office Action dated Mar. 20, 2024 in U.S. Appl. No. 17/163,177.
Non-Final Office Action dated Mar. 26, 2024 in U.S. Appl. No. 18/053,603.
Non-Final Office Action dated Mar. 28, 2024 in U.S. No. 17/531,555.
Non-Final Office Action dated Apr. 17, 2024 in U.S. Appl. No. 16/789,311.
Non-Final Office Action dated May 7, 2024 in U.S. Appl. No. 17/390,640.
Non-Final Office Action dated May 20, 2024 in U.S. Appl. No. 18/324,880.
Non-Final Office Action dated May 20, 2024 in U.S. Appl. No. 18/324,890.
Non-Final Office Action dated Jun. 14, 2024 in U.S. Appl. No. 16/525,054.
Notice of Allowability dated Mar. 7, 2023 for U.S. Appl. No. 17/147,272.
Notice of Allowance dated Jul. 7, 2017 in European Patent Application No. 13755319.4.
Notice of Allowance dated Jun. 14, 2018 in Singapore Patent Application No. 11201601188T.
Notice of Allowance dated Jul. 12, 2018 in Japanese Patent Application No. 2014-558975.
Notice of Allowance dated Sep. 24, 2018 in U.S. Appl. No. 16/038,887.
Notice of Allowance dated Sep. 24, 2018 in U.S. Appl. No. 16/038,979.
Notice of Allowance dated Apr. 1, 2019 in Singapore Patent Application No. 11201405274W.
Notice of Allowance dated Apr. 15, 2020 in U.S. Appl. No. 16/012,635.
Notice of Allowance dated Apr. 29, 2020 in U.S. Appl. No. 15/937,713.
Notice of Allowance dated Jun. 17, 2020 in European Patent Application No. 18195513.9.
Notice of Allowance dated Oct. 8, 2020 in Singapore application No. 11201901733P.
Notice of Allowance dated Jun. 18, 2021 in European Patent Application No. 17202409.3.
Notice of Allowance dated Feb. 23, 2023 in U.S. Appl. No. 17/320,052.
Notice of Allowance dated Feb. 24, 2023 in U.S. Appl. No. 17/183,840.
Notice of Allowance dated Sep. 29, 2023 in European Patent Application No. 22165594.7.
Notice of Allowance dated Nov. 16, 2023 in U.S. Appl. No. 16/677,012.
Notice of Allowance dated Dec. 5, 2023 in U.S. Appl. No. 17/373,519.
Notice of Allowance dated Dec. 6, 2023 in Korean Patent Application No. 10-2023-7012325.
Notice of Allowance dated Dec. 6, 2023 in U.S. Appl. No. 16/934,530.
Notice of Allowance dated Dec. 28, 2023 in U.S. Appl. No. 16/551,638.
Notice of Allowance Dated Jan. 20, 2024 in Chinese Patent Application No. 201911165393.0.
Notice of Allowance dated Jan. 24, 2024 in Israeli Patent Application No. 265478.
Notice of Allowance dated Mar. 20, 2024 in U.S. Appl. No. 18/190,884.
Notice of Allowance dated Mar. 20, 2024 in European Patent Application No. 21707112.5.
Notice of Allowance dated Apr. 8, 2024 in U.S. Appl. No. 16/846,133.
Notice of Allowance dated Apr. 25, 2024 in U.S. Appl. No. 16/848,241.
Notice of Allowance dated May 23, 2024 in Chinese Patent Application No. 201980037342.1.
Notice of Preliminary Rejection dated Feb. 23, 2024 for Korean Patent Application No. 10-2023- 7017312.
Office Action Dated Sep. 15, 2015 in Chinese Patent Application No. 201380022187.9.
Office Action Dated Oct. 10, 2017 in European Patent Application No. 14761937.3.
Office Action dated Jul. 30, 2018 in Japanese Patent Application No. 2016-537867.
Office Action dated Feb. 25, 2020 in Japanese Patent Application No. 2019-014564.
Office Action Dated Mar. 10, 2022 in Canadian Patent Application No. 2,865,575.
Office Action dated May 30, 2023 in Korean Patent Application No. 10-2023-7012325.
Office Action dated Jul. 10, 2023 in Japanese Patent Application No. 2022-096387.
Office Action dated Sep. 21, 2023 in Canadian Patent Application No. 3034924.
Office Action dated Jan. 31, 2024 in Chinese Patent Application No. 201980037342.1.
Office Action dated Feb. 1, 2024 in Japanese Patent Application No. 2021-507836.
Office Action dated Feb. 1, 2024 in Japanese Patent Application No. 2022-071002.
Office Action dated Feb. 13, 2024 in Japanese Patent Application No. 2022-525692.
Office Action dated Feb. 28, 2024 in Chinese Patent Application No. 202080014409.2.

(56) References Cited

OTHER PUBLICATIONS

Office Action dated Apr. 18, 2024 in Chinese Patent Application No. 201980082680.7.
Office Action dated Apr. 27, 2024 in Chinese Patent Application No. 202080048361.7.
Office Action dated Apr. 27, 2024 in Chinese Patent Application No. 2021980065685.9.
Office Action dated May 1, 2024 in Chinese Patent Application No. 201980070893.8.
Office Action dated May 17, 2024 in Chinese Patent Application No. 201980068704.3.
Office Action dated May 30, 2024 in Korean Patent Application No. 10-2022-7029623.
Office Action Dated May 31, 2024 in Chinese Patent Application No. 201980037175.0.
Office Action Dated Jun. 10, 2024 in Japanese Patent Application No. 2021-517856.
Office Action Dated Jun. 18, 2024 In Japanese Patent Application No. 2021-523956.
Schroder, "The Protein Puzzle", Biology & Medicine-Cell Research, 2017.
Spanova et al., "Magnetic hydrophilic methacrylate-based polymer microspheres designed for polymerase chain reaction applications", Journal of Chromatography vol. 800, 2004, 27-32.
Supplemental Notice of Allowability dated Apr. 2, 2024 in U.S. Appl. No. 18/190,884.
Tsompana et al., "Chromatin Accessibility: a window into the genome. Epigenetics & Chromatin" 2014 7:33.
Winter, E, Varshavsky A. A DNA binding protein that recognizes oligo(dA). oligo(dT) tracts. EMBO J. Jun. 1989;8(6):1867-77.
Wu, et al., "Time-resolved assessment of single-cell protein secretion by sequencing", bioRxiv, Dec. 21, 2021.

\* cited by examiner

1. Single cell samples are labeled with a unique bispecific (anchor/capture) probe.

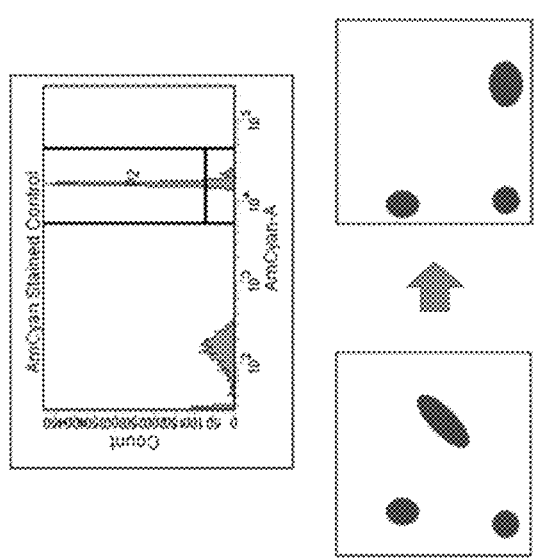

This can be a rapid (e.g. 5 min.) antibody labeling. Example anchor targets include ubiquitous immune system proteins such as CD44 or CD45.

2. Specific cell samples are then individually labeled with fluorescently conjugated antibodies.

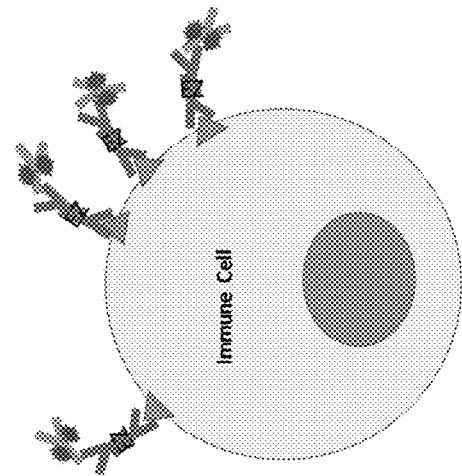

The capture arm of the bispecific probe can be a generic antibody with high affinity to all antibodies with specific host species (e.g., anti-mouse kappa light chain)

3. Cellular samples can now serve as brightly labeled single color fluorescence compensation particles.

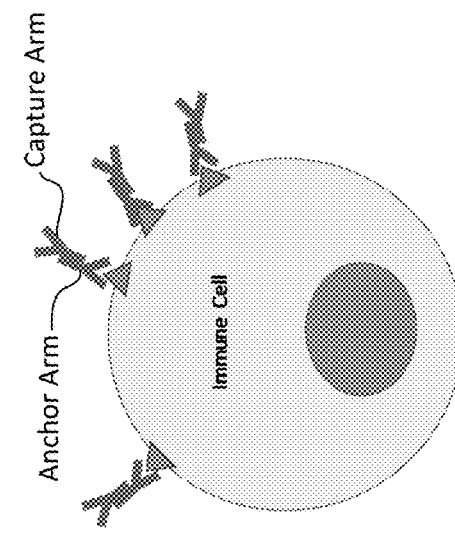

Single color control samples are a gold standard in nearly all multi-parameter flow cytometry experiments.

*FIG. 3*

BI-SPECIFIC PROBES TO ENABLE THE USE OF SINGLE-CELL SAMPLES AS SINGLE COLOR COMPENSATION CONTROL

RELATED APPLICATIONS

The present application claims priority under 35 U.S.C. § 119(e) to U.S. Provisional Application No. 62/981,479, filed Feb. 25, 2020; and U.S. Provisional Application No. 63/021,363, filed May 7, 2020. The entire contents of these applications are hereby expressly incorporated by reference in their entireties.

BACKGROUND

Field

The present disclosure relates generally to the field of detection assays using fluorescent detection reagents, for example fluorescent immunoassays, such as those carried out by flow cytometry, and more particularly to methods for reducing error in sample analysis.

Description of the Related Art

Particle analyzers, such as flow and scanning cytometers, are well known in the art. In these systems, fluorescently labeled particles, such as molecules, analyte-bound beads, or individual cells, are individually analyzed by exposing each particle to an excitation light, typically one or more lasers, and measuring the resulting fluorescence from each of dye labels. Each particle may be labeled with a multiplicity of spectrally distinct fluorescent dyes. Typically, detection is carried out using a multiplicity of photodetectors, one for each distinct dye to be detected. Both flow and scanning cytometers are commercially available from, for example, BD Biosciences (San Jose, Calif.). In a flow cytometer, for example, particles (such as molecules, analyte-bound beads, or individual cells) in a fluid suspension are passed through a detection region in which the particles are exposed to an excitation light, typically from one or more lasers, and the light scattering and fluorescence properties of the particles are measured. Markers, such as cell surface protein components of cells the presence of which can serve as a distinguishing characteristic, may be recognized by reagents (e.g., detection reagents) that include fluorescent dyes to facilitate detection, identification, and characterization. Each detection reagent can include a label, typically a fluorescent molecule or "dye," conjugated to a detector molecule that will selectively attach to a particular marker, for example, a monoclonal antibody. A multiplicity of different particles or components may be distinguished by using spectrally distinct fluorescent dyes to label the markers. In some implementations, a multiplicity of photodetectors is included in the analyzer. When a particle passes through the laser beam, time correlated pulses on forward scatter (FSC) and side scatter (SSC) detectors, and possibly also fluorescent emission detectors will occur. This is an "event," and for each event the magnitude of the detector output for each detector, FSC, SSC and fluorescent emission detectors is stored. The data obtained comprise the signals measured for each of the light scatter parameters and the fluorescence emissions.

Cytometers may further comprise components for storing the detector outputs and analyzing the data. For example, data storage and analysis may be carried out using a computer connected to the detection electronics. For example, the data can be stored logically in tabular form, where each row corresponds to data for one particle (or one event), and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include FSC, which refers to the excitation light that is scattered by the particle along a generally forward direction, SSC, which refers to the excitation light that is scattered by the particle in a generally sideways direction, and the light emitted from fluorescent molecules in one or more channels (frequency bands) of the spectrum, referred to as FL1, FL2, etc., or by the name of the fluorescent dye that emits primarily in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

In flow cytometers and other instruments that employ a multiplicity of photodetectors to detect a multiplicity of dyes, the collected light is separated into specific ranges of wavelengths, typically by a system of frequency-dependent filters and dichroic mirrors, such that the light detected by a particular photodetector is limited to a predefined range of wavelengths, referred to as a detection channel. The detection channels and dyes are selected such that the peak of the emission spectrum of each dye is within the frequency range of a different detection channel, e.g., each detection channel detects primarily the emission from a single dye. However, because of the breadth of the emission spectra of fluorescent dyes, typically a dye will fluoresce in more than one detection channels and, thus, measurements of dye fluorescence are not independent. The emission of one dye in detection channels intended for the detection of other dyes is referred to by a number of terms, such as spillover, spectral overlap, and crosstalk.

Methods of decreasing the effect of spectral overlap on dye fluorescence measurements are known in the art. Such methods involve adjustment of the signal measured by each photodetector by an amount calculated to compensate for the contribution from dyes other than the primary dye to be detected. Examples in the field of flow cytometry include Bagwell et al., 1993, "Fluorescence Spectral Overlap Compensation for any Number of Flow Cytometer Parameters", Ann. N.Y. Acad. Sci. 677: 167-184; Roederer et al., 1997, "Eight Color, 10-Parameter Flow Cytometry to Elucidate Complex Leukocyte Hetrogeneity", Cytometry 29: 328-339; and Bigos et al., 1999, Cytometry 36: 36-45; Verwer, 2002, BD FACSDiVa™ Option for the BD FACSVantage SE Flow Cytometer White Paper, and U.S. Pat. No. 6,897,954; each incorporated herein by reference. WinList™ (Verity Software House, Topsham, Me.) and FlowJo 5.7.2 software (Tree Star, Inc., Ashland, Oreg.) are a stand-alone software packages that allow software compensation on stored data files produced by a flow cytometer.

Typically, the amount of fluorescence spectral overlap compensation required is determined experimentally using compensation control beads, single-color particles dye with one of the fluorescent dyes used in the assay. The fluorescence signal of each bead is measured in each of the channels, which directly provides a measure of the spectral overlap into each of the channels. One method of measuring spectral overlap of fluorescently labeled antibody reagents (e.g., detection reagents) into each of the detection channels is using BD™ CompBeads compensation particles (BD Biosciences, San Jose, Calif.). The particles, which are coated with anti-Ig antibodies, are combined with a fluorescently labeled antibody reagent, which becomes captured on the surface of the bead, to produce a particle labeled with the fluorescent dye. The spectral overlap of the dye is determined by measuring the emission of the labeled particle in each of the detection channels. The measurement typically is made relative to the emission from the unlabeled particle. There is a need for methods and compositions that can improve spectral unmixing and compensation (and thereby improve resolution) in multi-parameter flow cytometry.

SUMMARY

Disclosed herein include methods for determining spillover. In some embodiments, the method comprises: providing cells associated with a bispecific reagent and a first detection reagent, wherein the bispecific reagent comprises an anchor probe capable of specifically binding a cell surface target and a capture probe capable of specifically binding to the first detection reagent comprising a first label, wherein the emission spectrum of the first label comprises a first emission wavelength range and a first peak emission wavelength; providing an instrument comprising a first detector and a second detector, wherein the first detector is capable of detecting emissions within a first detection wavelength range and the second detector is capable of detecting emissions within a second detection wavelength range, wherein the first peak emission wavelength is within the first detection wavelength range and not within the second detection wavelength range, wherein a portion of the first emission wavelength range overlaps with the second detection wavelength range; and measuring, for one or more events of the cells associated with the bispecific reagent and the first detection reagent, emissions in the first detector to obtain a first reference value and emissions in the second detector to obtain a second reference value, wherein spillover comprises the second reference value. In some embodiments, the capture probe is capable of specifically binding to a second detection reagent, the method comprising: providing cells associated with the bispecific reagent and a second detection reagent comprising a second label; and measuring, for one or more events of the cells associated with the bispecific reagent and the second detection reagent, emissions in the first detector to obtain a third reference value and emissions in the second detector to obtain a fourth reference value.

Disclosed herein include methods for performing a multi-label experiment on an instrument comprising a first detector and a second detector. In some embodiments, the method comprises: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target, and wherein the second detection reagent is capable of specifically binding to the second cell target; providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; providing an instrument comprising a first detector and a second detector; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; measuring, for one or more events of the cells associated with the first detection reagent and the second detection reagent, emissions in the first detector to obtain a first experimental value and emissions in the second detector to obtain a second experimental value; and measuring, for one or more events of a plurality of unlabeled cells, emissions in the first detector to obtain a first background emission value and emissions in the second detector to obtain a second background emission value.

Disclosed herein include methods for performing compensation. In some embodiments, the method comprises: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target and the second detection reagent is capable of specifically binding to the second cell target; providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; providing an instrument comprising a first detector and a second detector; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; measuring, for one or more events of the cells associated with the first detection reagent and the second detection reagent, emissions in the first detector to obtain a first experimental value and emissions in the second detector to obtain a second experimental value; measuring, for one or more events of a plurality of unlabeled cells, emissions in the first detector to obtain a first background emission value and emissions in the second detector to obtain a second background emission value; and adjusting, for the one or more events of the cells associated with the first detection reagent and the second detection reagent, the first experimental value and/or the second experimental value based on one or more of the first, second, third, and fourth reference values and/or one or more of the first and second background emission values.

The method can comprise: generating a compensation matrix based on one or more of the first, second, third, and fourth reference values. The method can comprise: generating a compensation matrix based on one or more of the first, second, third, and fourth reference values and one or more of the first and second background emission values.

Disclosed herein include methods for generating a compensation matrix for an instrument for analyzing a plurality of labels using a plurality of detectors. In some embodiments, the method comprises: providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; and generating a compensation matrix based on one or more of the first, second, third, and fourth reference values.

In some embodiments, generating a compensation matrix based on one or more of the first, second, third, and fourth reference values comprises: measuring, for one or more events of a plurality of unlabeled cells, emissions in the first detector to obtain a first background emission value and emissions in the second detector to obtain a second background emission value; and generating a compensation matrix based on one or more of the first, second, third, and fourth reference values and one or more of the first and second background emission values. In some embodiments, providing cells associated with a bispecific reagent and a first detection reagent comprises: contacting a plurality of control cells comprising a cell surface target with the bispecific reagent to form cells associated with the bispecific reagent, wherein the bispecific reagent comprises an anchor probe capable of specifically binding to the cell surface target, and wherein the bispecific reagent comprises a capture probe capable of specifically binding to the first detection reagent and/or the second detection reagent; and contacting the first detection reagent with cells associated with the bispecific reagent to form cells associated with the bispecific reagent and the first detection reagent. In some embodiments, providing cells associated with a bispecific reagent and a second detection reagent comprises: contacting a plurality of control cells comprising a cell surface target with the bispecific reagent to form cells associated with the bispecific reagent, wherein the bispecific reagent comprises an anchor probe capable of specifically binding to the cell surface target, and wherein the bispecific reagent comprises a capture probe capable of specifically binding to the first detection reagent and/or the second detection reagent; and contacting the second detection reagent with cells associated with the bispecific reagent to form cells associated with the bispecific reagent and the second detection reagent.

The method can comprise: measuring, for one or more events of a plurality of unlabeled cells, emissions in the first detector to obtain a first background emission value and emissions in the second detector to obtain a second background emission value. The method can comprise: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target, and wherein the second detection reagent is capable of specifically binding to the second cell target; and measuring, for one or more events of the cells associated with the first detection reagent and the second detection reagent, emissions in the first detector to obtain a first experimental value and emissions in the second detector to obtain a second experimental value. The method can comprise: adjusting, for the one or more events of the cells associated with the first detection reagent and the second detection reagent, the first experimental value and/or the second experimental value based on one or more of the first, second, third, and fourth reference values and/or one or more of the first and second background emission values.

The method can comprise: adjusting, for the one or more events of the cells associated with the first detection reagent and the second detection reagent, the first experimental value and/or the second experimental value based on a spillover matrix and/or a compensation matrix. In some embodiments, generating a compensation matrix based on one or more of the first, second, third, and fourth reference values comprises: generating a spillover matrix based on one or more of the first, second, third, and fourth reference values. The method can comprise: generating a spillover matrix based on one or more of the first, second, third, and fourth reference values. The method can comprise: generating a spillover matrix based on one or more of the first, second, third, and fourth reference values and/or one or more of the first and second background emission values. The method can comprise: generating a compensation matrix based on a spillover matrix. In some embodiments, the compensation matrix is the inverse of the spillover matrix. In some embodiments, the compensation matrix is stored in the instrument for subsequent use. In some embodiments, spillover comprises emissions of the first label detected by the second detector and/or emissions of the second label detected by the first detector.

In some embodiments, the plurality of control cells, the plurality of unlabeled cells, and/or the plurality of sample cells are derived from the same cell sample. In some embodiments, the plurality of control cells, the plurality of unlabeled cells, and/or the plurality of sample cells comprise a plurality of single cells. In some embodiments, the plurality of control cells, the plurality of unlabeled cells, and/or the plurality of sample cells comprise a heterogeneous cell population. In some embodiments, the plurality of control cells, the plurality of unlabeled cells, and/or the plurality of sample cells comprise two or more cell types. In some embodiments, one or more events comprises about 10 events to about 100,000 events. In some embodiments, the plurality of unlabeled cells is not associated with a first detection reagent or a second detection reagent. In some embodiments, the plurality of unlabeled cells is not associated with a label. In some embodiments, the plurality of unlabeled cells is not associated with a fluorophore.

In some embodiments, the emissions in the first detector of the one or more events of the cells associated with the bispecific reagent and the first detection reagent are as high as the emissions in the first detector of the one or more events of the cells associated with the first detection reagent and the second detection reagent. In some embodiments, the emissions in the first detector of the one or more events of the cells associated with the bispecific reagent and the first detection reagent are at least about 5% higher than the emissions in the first detector of the one or more events of the cells associated with the first detection reagent and the second detection reagent. In some embodiments, the emissions in the second detector of the one or more events of the cells associated with the bispecific reagent and the second detection reagent are as high as the emissions in the second detector of the one or more events of the cells associated with the first detection reagent and the second detection reagent. In some embodiments, the emissions in the second detector of the one or more events of the cells associated with the bispecific reagent and the second detection reagent are at least about 5% higher than the emissions in the second detector of the one or more events of the cells associated with the first detection reagent and the second detection reagent.

In some embodiments, the instrument comprises a flow cytometer. In some embodiments, the flow cytometer comprises a conventional flow cytometer. In some embodiments, the flow cytometer comprises spectral flow cytometer, a hyperspectral flow cytometer, an imaging flow cytometer, or any combination thereof. In some embodiments, the instrument comprises a multi-fluorescence imaging system. In some embodiments, the instrument comprises a fluorescence microscope. In some embodiments, the instrument comprises a protein array. In some embodiments, the measuring comprises performing an immunohistochemistry assay. In some embodiments, the measuring comprises performing an enzyme-linked immunosorbent assay (ELISA). In some embodiments, first detector and/or second detector is paired with one or more filters. In some embodiments, the one or more filters comprise a long pass filter, a short pass filter, a band pass filter, or any combination thereof. In some embodiments, the instrument comprises one or more excitation lasers. In some embodiments, the first detector and/or second detector comprise photodetectors. In some embodiments, the first detector and/or second detector comprise fluorescence emission detectors. In some embodiments, the first label and/or the second label comprise a fluorophore. In some embodiments, the emissions comprise fluorescence emissions. In some embodiments, one or more of the first, second, third, and fourth reference values, one or more of the first and second background emission values, and/or one or more of the first and second experimental values comprise a fluorescence intensity value. In some embodiments, one or more of the first, second, third, and fourth reference values, one or more of the first and second background emission values, and/or one or more of the first and second experimental values comprise a mean fluorescence intensity value. In some embodiments, one or more of the first, second, third, and fourth reference values, one or more of the first and second background emission values, and/or one or more of the first and second experimental values comprise a median fluorescence intensity value. In some embodiments, first background emission value and/or the second background emission value comprise autofluorescence. In some embodiments, the first detection reagent comprises a third label, wherein the first label and third label are capable of fluorescence resonance energy transfer (FRET) when brought in close proximity. In some embodiments, the first label and the third label comprise tandem dyes.

In some embodiments, the emission spectrum of the first label comprises a first emission wavelength range and a first peak emission wavelength. In some embodiments, the emission spectrum of the second label comprises a second emission wavelength range and a second peak emission wavelength. In some embodiments, the first detector is capable of detecting emissions within a first detection wavelength range. In some embodiments, the second detector is capable of detecting emissions within a second detection wavelength range. In some embodiments, the second emission wavelength range is different from the first detection wavelength range. In some embodiments, the second peak emission wavelength is different from the first peak emission wavelength. In some embodiments, the first emission wavelength range is different from the second detection wavelength range. In some embodiments, the first peak emission wavelength range is different from the second peak emission wavelength range. In some embodiments, a portion of the first emission wavelength range overlaps with the second detection wavelength range. In some embodiments, a portion of the second emission wavelength range overlaps with the first detection wavelength range. In some embodiments, the first peak emission wavelength is within the first detection wavelength range, and wherein the first peak emission wavelength is not within the second detection wavelength range. In some embodiments, the second peak emission wavelength is within the second detection wavelength range, and wherein the second peak emission wavelength is not within the first detection wavelength range. In some embodiments, the first detector is the primary detector of the first label and wherein the second detector is the secondary detector of the first label. In some embodiments, the second detector is the primary detector of the second label and wherein the first detector is the secondary detector of the second label.

In some embodiments, the instrument comprises a forward scatter detector and a side scatter detector. The method can comprise: measuring, for one or more events of the unlabeled cells, for one or more events of the cells associated with the bispecific reagent and the first detection reagent and/or for one or more events of the cells associated with the bispecific reagent and the second detection reagent, a forward scatter value and a side scatter value. The method can comprise: determining forward scatter-side scatter plot locations of one or more events of the unlabeled cells, of one or more events of the cells associated with the bispecific reagent and the first detection reagent, and/or of one or more events of the cells associated with the bispecific reagent and the second detection reagent based on the forward scatter value and the side scatter value. The method can comprise: associating the forward scatter-side scatter plot locations of one or more events of the unlabeled cells, of one or more events of the cells associated with the bispecific reagent and the first detection reagent, and/or of one or more events of the cells associated with the bispecific reagent and the second detection reagent with forward scatter-side scatter plot regions. In some embodiments, a forward scatter-side scatter plot region comprises a plurality of adjacent forward scatter-side scatter plot locations. In some embodiments, a forward scatter-side scatter plot region comprises the forward scatter-side scatter plot locations of about 10 events to about 100,000 events. In some embodiments, the events of cells of the same cell type are associated with the same forward scatter-side scatter plot region. In some embodiments, the events of cells of the different cell types are associated with the different forward scatter-side scatter plot regions. In some embodiments, the two or more cell types are associated with different forward scatter-side scatter plot regions.

The method can comprise: associating the first reference value and/or the second reference value of one or more events of the cells associated with the bispecific reagent and the first detection reagent with one or more forward scatter-side scatter plot regions. The method can comprise: associating the third reference value and/or the fourth reference value of one or more events of the cells associated with the bispecific reagent and the second detection reagent with one or more forward scatter-side scatter plot regions. The method can comprise: associating the first background emission value and/or the second background emission value of one or more events of the unlabeled cells with one or more forward scatter-side scatter plot regions. The method can comprise: generating a spillover matrix and/or a compensation matrix for one or more forward scatter-side scatter plot regions based on one or more of the first, second, third, and fourth reference values and/or one or more of the first and second background emission values associated with the respective forward scatter-side scatter plot regions. The method can comprise: measuring, for one or more events of the cells associated with the first detection reagent and the second detection reagent, a forward scatter value and a side scatter value. The method can comprise: determining the forward scatter-side scatter plot locations of one or more events of the cells associated with the first detection reagent and the second detection reagent based on the forward scatter value and the side scatter value. The method can comprise: associating the forward scatter-side scatter plot locations of one or more events of the cells associated with the first detection reagent and the second detection reagent with forward scatter-side scatter plot regions. The method can comprise: adjusting, for the one or more events of the cells associated with the first detection reagent and the second detection reagent, the first experimental value and/or the second experimental value based on the one or more of the first, second, third, and fourth reference values and/or one or more of the first and second background emission values associated with the respective forward scatter-side scatter plot regions. The method can comprise: adjusting, for the one or more events of the cells associated with the first detection reagent and the second detection reagent, the first experimental value and/or the second experimental value based on the spillover matrix and/or compensation matrix associated with the respective forward scatter-side scatter plot region.

In some embodiments, the use of the bispecific reagent increases resolution sensitivity by at least about five percent as compared to a comparable method that does not employ the bispecific reagent, wherein resolution sensitivity comprises the ability of the instrument to differentiate between dimly labeled cells and unlabeled cells. In some embodiments, dimly labeled cells comprise cells associated with the first detection reagent and the second detection reagent for which the first experimental value is less than about 50%, about 40%, about 30%, about 20%, about 10%, or about 5%, greater than the first background emission value. In some embodiments, dimly labeled cells comprise cells associated with the first detection reagent and the second detection reagent for which the second experimental value is less than about 50%, about 40%, about 30%, about 20%, about 10%, or about 5%, greater than the second background emission value. In some embodiments, the comparable method employs compensation beads. In some embodiments, the comparable method employs compensation beads to generate a spillover matrix and/or a compensation matrix. In some embodiments, the compensation beads comprise BD CompBeads, OneComp beads, UltraComp beads, VersaComp beads, or any combination thereof.

In some embodiments, one or more of the first detection reagent, the second detection reagent, the bispecific reagent, the capture probe, and the anchor probe comprise an antibody or fragment thereof. In some embodiments, the capture probe is capable of specifically binding to a light chain constant domain and/or a heavy chain constant domain. In some embodiments, the first detection reagent and/or the second detection reagent comprises a heavy chain constant domain and/or a light chain constant domain. In some embodiments, the heavy chain constant domain comprises the constant domains of IgG1, IgG2, IgG3, IgG4, IgM, IgA1, IgA2, IgD, IgE, or any combination thereof. In some embodiments, the light chain constant domain is a lambda light chain constant domain. In some embodiments, the light chain constant domain is a kappa light chain constant domain. In some embodiments, the antibody or fragment thereof is derived from a mouse, rat, guinea pig, hamster, rabbit, cat, dog, monkey, cow, pig, horse, goat, sheep, or any combination thereof. In some embodiments, the bispecific reagent comprises a conjugate of an antibody or fragment thereof and an antibody or fragment thereof. In some embodiments, the antibody or fragment thereof comprises a monoclonal antibody. In some embodiments, the antibody or fragment thereof is conjugated to the antibody or fragment thereof via chemical coupling, genetic fusion, noncovalent association, or any combination thereof. In some embodiments, the conjugate is formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. In some embodiments, the conjugate is formed by a reaction between acetylene and azide. In some embodiments, the conjugate is formed by a reaction between an aldehyde or ketone group and a hydrazine or alkoxy amine. In some embodiments, the antibody or fragment thereof comprises a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The method can comprise: determining one or more characteristics of the sample cells based on the first experimental value and/or the second experimental value of one or more events of the cells associated with the first detection reagent and the second detection reagent. In some embodiments, the more of more characteristics comprise the number of copies of the first cell target and/or the second cell target in one or more of the plurality of sample cells. In some embodiments, the first cell target and/or second cell target comprise a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. In some embodiments, the first cell target and/or second cell target is on a cell surface.

In some embodiments, the cell surface target comprises a carbohydrate, a lipid, a protein, or any combination thereof. In some embodiments, the cell surface target comprises CD1a, CD1b, CD1c, CD1d, CD1e, CD2, CD3, CD3d, CD3e, CD3g, CD4, CD5, CD6, CD7, CD8a, CD8b, CD9, CD10, CD11a, CD11b, CD11c, CD11d, CDw12, CD13, CD14, CD15, CD15u, CD15s, CD15su, CD16, CD16b, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45RA, CD45RB, CD45RC, CD45RO, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CD75, CD75s, CD77, CD79a, CD79b, CD80, CD81, CD82, CD83, CD84, CD85a, CD85d, CD85j, CD85k, CD86, CD87, CD88, CD89, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140a, CD140b, CD141, CD142, CD143, CD144, CDw145, CD146, CD147, CD148, CDw149, CD150, CD151, CD152, CD153, CD154, CD155, CD156a, CD156b, CD156c, CD157, CD158e, CD158i, CD158k, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CDw198, CD199, CD200, CD201, CD202b, CD203c, CD204, CD205, CD206, CD207, CD208, CD209, CD210, CDw210b, CD212, CD213a1, CD213a2, CD215, CD217a, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240DCE, CD240D, CD241, CD242, CD243, CD244, CD245, CD246, CD247, CD248, CD249, CD252, CD253, CD254, CD256, CD266, CD267, CD268, CD269, CD270, CD271, CD272, CD273, CD274, CD275, CD276, CD277, CD278, CD279, CD280, CD281, CD282, CD283, CD284, CD286, CD289, CD290, CD292, CDw293, CD294, CD295, CD296, CD297, CD298, CD299, CD300a, CD300c, CD300e, CD301, CD302, CD303, CD304, CD305, CD306, CD307a, CD307b, CD307c, CD307d, CD307e, CD308, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362, CD363, CD364, CD365, CD366, CD367, CD368, CD369, CD370, CD371, BCMA, a HLA protein, β2-microglobulin, or any combination thereof. In some embodiments, the cell surface target is at least about 2-fold more abundant than the first cell target and/or the second cell target.

In some embodiments, the bispecific reagent comprises a plurality of bispecific reagents. In some embodiments, the plurality of bispecific reagents comprises identical bispecific reagents. In some embodiments, the plurality of bispecific reagents comprises a mixture of two or more distinct bispecific reagents. In some embodiments, the bispecific reagent comprises a bispecific reagent composition comprising a mixture of two or more distinct bispecific reagents. In some embodiments, the two or more distinct bispecific reagents are capable of specifically binding to distinct detection reagents. In some embodiments, the two or more distinct bispecific reagents are capable of specifically binding to distinct cell surface targets. The method can comprise: after contacting the plurality of bispecific reagents with the plurality of control cells, removing one or more bispecific reagents of the plurality of bispecific reagents that are not contacted with the plurality of control cells. In some embodiments, removing the one or more bispecific reagents not contacted with the plurality of control cells comprises: removing the one or more bispecific reagents not contacted with the cell surface target.

In some embodiments, the first detection reagent comprises a plurality of the first detection reagents and/or wherein the second detection reagent comprises a plurality of the second detection reagents. The method can comprise: after contacting the plurality of first detection reagents and the plurality of second detection reagents with a plurality of sample cells, removing one or more first detection reagents and one or more second detection reagents of the plurality of first detection reagents and plurality of second detection reagents that are not contacted with the plurality of sample cells. In some embodiments, removing one or more first detection reagents and one or more second detection reagents of the plurality of first detection reagents and plurality of second detection reagents that are not contacted with the plurality of sample cells comprises: removing the one or more first detection reagents and the one or more second detection reagents not contacted with the first cell target and the second cell target, respectively. The method can comprise: after contacting the plurality of first detection reagents with the cells associated with the bispecific reagent, removing one or more first detection reagents of the plurality of first detection reagents that are not contacted with the cells associated with the bispecific reagent. In some embodiments, removing one or more first detection reagents of the plurality of first detection reagents that are not contacted with the cells associated with the bispecific reagent comprises: removing the one or more first detection reagents not contacted with the bispecific reagent. The method can comprise: after contacting the plurality of second detection reagents with the cells associated with the bispecific reagent, removing one or more second detection reagents of the plurality of second detection reagents that are not contacted with the cells associated with the bispecific reagent. In some embodiments, removing one or more second detection reagents of the plurality of second detection reagents that are not contacted with the cells associated with the bispecific reagent comprises: removing the one or more second detection reagents not contacted with the bispecific reagent.

Disclosed herein include compositions. In some embodiments, the composition comprises: a cell associated with a bispecific reagent, wherein the bispecific reagent comprises an anchor probe specifically bound to a cell surface target on the cell and a capture probe capable of specifically binding to a detection reagent. In some embodiments, the detection reagent is capable of specifically binding to a cell target, and wherein the cell surface target is at least about 2-fold more abundant than the cell target. In some embodiments, one or more of the bispecific reagent, the detection reagent, the capture probe, and/or the anchor probe comprise an antibody or fragment thereof. In some embodiments, the capture probe is capable of specifically binding to a light chain constant domain and/or a heavy chain constant domain. In some embodiments, the detection reagent comprises a heavy chain constant domain and/or a light chain constant domain, optionally wherein the detection reagent comprises a fluorophore. In some embodiments, the heavy chain constant domain comprises the constant domains of IgG1, IgG2, IgG3, IgG4, IgM, IgA1, IgA2, IgD, IgE, or any combination thereof. In some embodiments, the light chain constant domain comprises a lambda light chain constant domain and/or a kappa light chain constant domain. In some embodiments, the bispecific reagent comprises a conjugate of an antibody or fragment thereof and an antibody or fragment thereof. In some embodiments, the antibody or fragment thereof is conjugated to the antibody or fragment thereof via chemical coupling, genetic fusion, noncovalent association, or any combination thereof. In some embodiments, the conjugate is formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. In some embodiments, the conjugate is formed by a reaction between acetylene and azide. In some embodiments, the conjugate is formed by a reaction between an aldehyde or ketone group and a hydrazine or alkoxy amine. In some embodiments, the antibody or fragment thereof comprises a monoclonal antibody, a Fab, a Fab', a F(ab')$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

BRIEF DESCRIPTION OF THE DRAWINGS

FIG. 3 depicts a non-limiting exemplary compensation workflow for multi-parameter flow cytometry.

DETAILED DESCRIPTION

Figure 1:
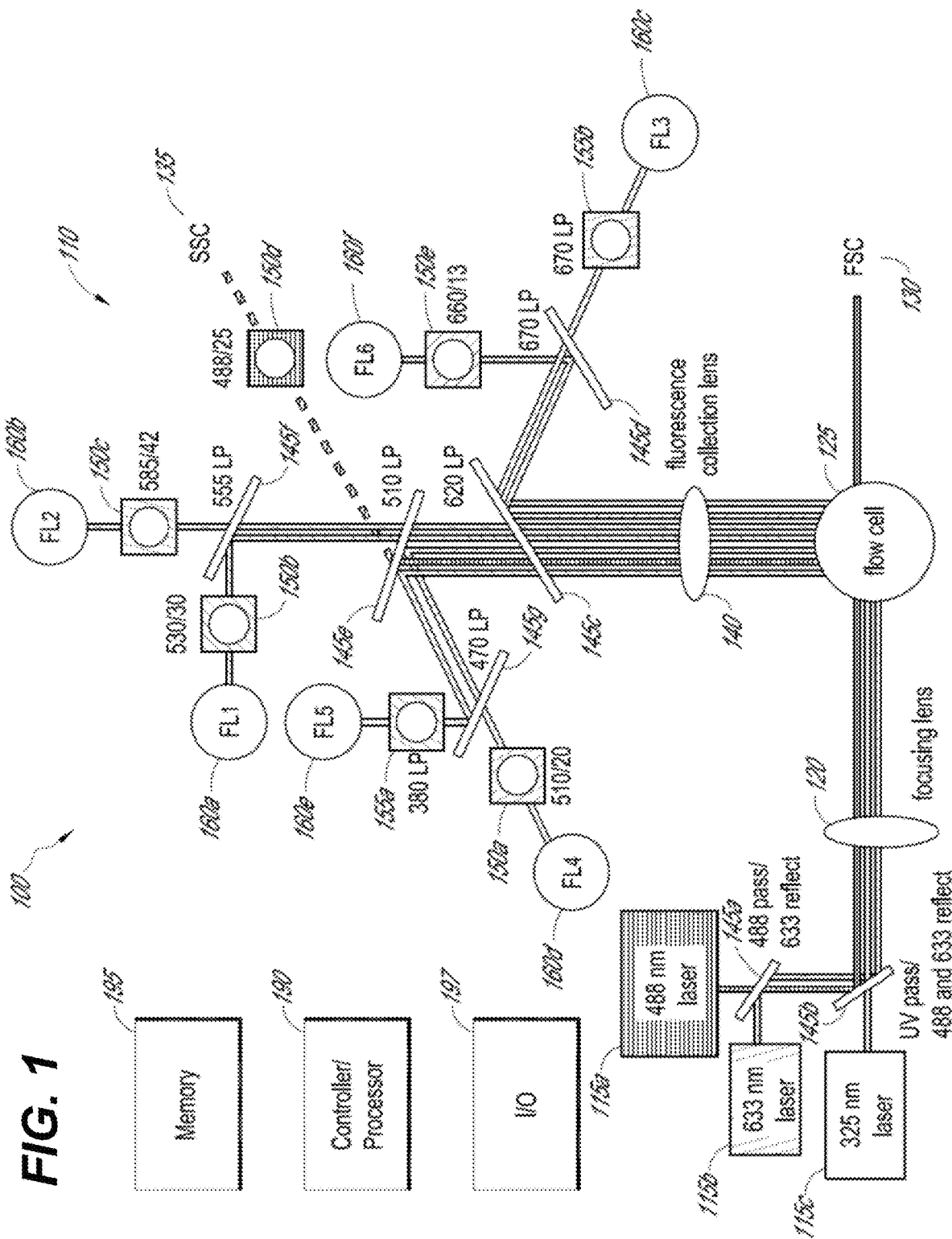
FIG. 1 depicts a non-limiting exemplary flow cytometer employed in the methods and compositions provided herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989).

FIG. 1 shows a system 100 for flow cytometry in accordance with an illustrative embodiment of the methods and compositions provided herein. The system 100 includes a flow cytometer 110, a controller/processor 190 and a memory 195. The flow cytometer 110 includes one or more excitation lasers 115a-c, a focusing lens 120, a flow chamber 125, a forward scatter detector 130, a side scatter detector 135, a fluorescence collection lens 140, one or more beam splitters 145a-g, one or more bandpass filters 150a-e, one or more longpass ("LP") filters 155a-b, and one or more fluorescent emission detectors 160a-f.

The excitation lasers 115a-c emit light in the form of a laser beam. The wavelengths of the laser beams emitted from excitation lasers 115a-c are 488 nm, 633 nm, and 325 nm, respectively, in the example system of FIG. 1. The laser beams are first directed through one or more of beam splitters 145a and 145b. Beam splitter 145a transmits light at 488 nm and reflects light at 633 nm. Beam splitter 145b transmits UV light (light with a wavelength in the range of 10 to 400 nm) and reflects light at 488 nm and 633 nm.

The laser beams are then directed to a focusing lens 120, which focuses the beams onto the portion of a fluid stream where particles of a sample are located, within the flow chamber 125. The flow chamber is part of a fluidics system which directs particles, typically one at a time, in a stream to the focused laser beam for interrogation. The flow chamber can comprise a flow cell in a benchtop cytometer or a nozzle tip in a stream-in-air cytometer.

The light from the laser beam(s) interacts with the particles in the sample by diffraction, refraction, reflection, scattering, and absorption with re-emission at various different wavelengths depending on the characteristics of the particle such as its size, internal structure, and the presence of one or more fluorescent molecules attached to or naturally present on or in the particle. The fluorescence emissions as well as the diffracted light, refracted light, reflected light, and scattered light may be routed to one or more of the forward scatter detector 130, the side scatter detector 135, and the one or more fluorescent emission detectors 160a-f through one or more of the beam splitters 145a-g, the bandpass filters 150a-e, the longpass filters 155a-b, and the fluorescence collection lens 140.

The fluorescence collection lens 140 collects light emitted from the particle-laser beam interaction and routes that light towards one or more beam splitters and filters. Bandpass filters, such as bandpass filters 150a-e, allow a narrow range of wavelengths to pass through the filter. For example, bandpass filter 150a is a 510/20 filter. The first number represents the center of a spectral band. The second number provides a range of the spectral band. Thus, a 510/20 filter extends 10 nm on each side of the center of the spectral band, or from 500 nm to 520 nm. Shortpass filters transmit wavelengths of light equal to or shorter than a specified wavelength. Longpass filters, such as longpass filters 155a-b, transmit wavelengths of light equal to or longer than a specified wavelength of light. For example, longpass filter 155a, which is a 670 nm longpass filter, transmits light equal to or longer than 670 nm. Filters are often selected to optimize the specificity of a detector for a particular fluorescent dye. The filters can be configured so that the spectral band of light transmitted to the detector is close to the emission peak of a fluorescent dye.

Beam splitters direct light of different wavelengths in different directions. Beam splitters can be characterized by filter properties such as shortpass and longpass. For example, beam splitter 145g is a 620 SP beam splitter, meaning that the beam splitter 145g transmits wavelengths of light that are 620 nm or shorter and reflects wavelengths of light that are longer than 620 nm in a different direction. In one embodiment, the beam splitters 145a-g can comprise optical mirrors, such as dichroic mirrors.

The forward scatter detector 130 is positioned slightly off axis from the direct beam through the flow cell and is configured to detect diffracted light, the excitation light that travels through or around the particle in mostly a forward direction. The intensity of the light detected by the forward scatter detector is dependent on the overall size of the particle. The forward scatter detector can include a photodiode. The side scatter detector 135 is configured to detect refracted and reflected light from the surfaces and internal structures of the particle, and tends to increase with increasing particle complexity of structure. The fluorescence emissions from fluorescent molecules associated with the particle can be detected by the one or more fluorescent emission detectors 160a-f. The side scatter detector 135 and fluorescent emission detectors can include photomultiplier tubes. The signals detected at the forward scatter detector 130, the side scatter detector 135 and the fluorescent emission detectors can be converted to electronic signals (voltages) by the detectors. This data can provide information about the sample.

One of skill in the art will recognize that a flow cytometer in accordance with an embodiment of the disclosed methods and compositions is not limited to the flow cytometer depicted in FIG. 1, but can include any flow cytometer known in the art. For example, a flow cytometer may have any number of lasers, beam splitters, filters, and detectors at various wavelengths and in various different configurations.

In operation, cytometer operation is controlled by a controller/processor 190, and the measurement data from the detectors can be stored in the memory 195 and processed by the controller/processor 190. Although not shown explicitly, the controller/processor 190 is coupled to the detectors to receive the output signals therefrom, and may also be coupled to electrical and electromechanical components of the flow cytometer 100 to control the lasers, fluid flow parameters, and the like. Input/output (I/O) capabilities 197 may be provided also in the system. The memory 195, controller/processor 190, and I/O 197 may be entirely provided as an integral part of the flow cytometer 110. In such an embodiment, a display may also form part of the I/O capabilities 197 for presenting experimental data to users of the cytometer 100. Alternatively, some or all of the memory 195 and controller/processor 190 and I/O capabilities may be part of one or more external devices such as a general purpose computer. In some embodiments, some or all of the memory 195 and controller/processor 190 can be in wireless or wired communication with the cytometer 110. The controller/processor 190 in conjunction with the memory 195 and the I/O 197 can be configured to perform various functions related to the preparation and analysis of a flow cytometer experiment.

The system of FIG. 1 includes six different detectors that detect fluorescent light in six different wavelength bands (which may be referred to herein as a "filter window" or "fluorescence channel" for a given detector) as defined by the configuration of filters and/or splitters in the beam path from the flow cell 125 to each detector. Different fluorescent molecules used for a flow cytometer experiment will emit light in their own characteristic wavelength bands. The particular fluorescent labels used for an experiment and their associated fluorescent emission bands may be selected to generally coincide with the filter windows of the detectors. However, as more detectors are provided, and more labels are utilized, perfect correspondence between filter windows and fluorescent emission spectra is not possible. It is generally true that although the peak of the emission spectra of a particular fluorescent molecule may lie within the filter window of one particular detector, some of the emission spectra of that label will also overlap the filter windows of one or more other detectors. This may be referred to as spillover.

The I/O 197 can be configured to receive data regarding a flow cytometer experiment having a panel of fluorescent labels and a plurality of cell populations having a plurality of markers, each cell population having a subset of the plurality of markers. The I/O 197 can also be configured to receive biological data assigning one or more markers to one or more cell populations, marker density data, emission spectrum data, data assigning labels to one or more markers, and cytometer configuration data. Flow cytometer experiment data, such as label spectral characteristics and flow cytometer configuration data can also be stored in the memory 195. The controller/processor 190 can be configured to evaluate one or more assignments of labels to markers.

Figure 2:
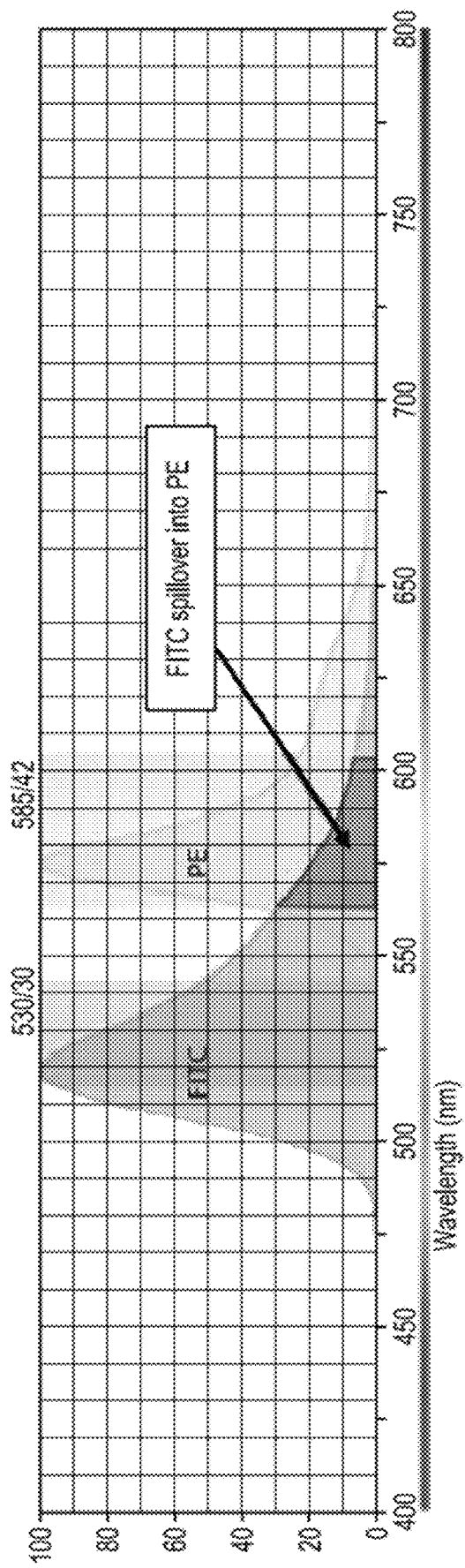
FIG. 2 depicts a non-limiting exemplary graph of the emission spectra of labels and the filter windows of photodetectors employed in the methods and compositions provided herein.

FIG. 2 shows an illustrative example of spillover (e.g., spectral overlap) caused by overlapping emissions spectra for different labels. FIG. 2 shows the emission spectra of markers labeled with FITC, represented by the curve extending from a wavelength of approximately 475 nm to 650 nm, and the filter window for a "FITC detector." One or more filters, such as bandpass filter 150b as depicted in FIG. 1, can be placed in front of the detector, limiting the range of wavelengths that can reach the detector, the range of wavelengths constituting a filter window. The filter window for the FITC detector is 530/30, meaning that the filter window extends from 515 nm to 545 nm. The FITC filter window is represented by the shaded rectangle extending from 515 nm to 545 nm. FIG. 2 also shows the emission spectra of markers labeled with PE, represented by the curve extending from approximately 525 nm to approximately 725 nm. One or more filters, such as bandpass filter 150c as depicted in FIG. 1, can be placed in front of the detector. The filter window for the PE detector is 585/42, meaning that the filter window extends from 564 nm to 606 nm. The PE filter window is represented by the shaded rectangle extending from 564 nm to 606 nm. FIG. 2 illustrates that a portion of the emissions spectra for FITC overlaps the filter window for the PE detector, labeled as "FITC spillover into PE." Therefore, some of the fluorescence emission of the FITC label is detected in the PE detector and measured along with the fluorescence emission of the PE label. Spillover can cause inaccurate conclusions to be drawn regarding the abundance of labels present on a particle. This problem can be especially acute for recent uses of flow cytometers as more labels and detectors are utilized, which reduces the separation of fluorescent peaks and filter windows. Given also the increasing number of fluorescent labels available (generally dozens of options are available to an experimenter), with a variety of peak wavelengths, emission intensities and energies, and spectral width characteristics, the variety of marker densities on cells being characterized, as well as in some cases selectable filter windows, it is very challenging to design a suitable set up for a flow cytometer experiment. A further complication is the autofluorescence of cells or other particles being characterized. This autofluorescence signal will also overlap one or more filter windows causing noise in the measurements. The autofluorescence noise signal can further be dependent on the type of particle/cell being interrogated.

In some embodiments, to take spillover across multiple detectors for multiple labels into account, spectral overlap values may be characterized for all labels in all detectors through each respective filter window. For example, at each detection event, the response of a given detector can be the sum of the products of the overlap of the given detector filter window with each label multiplied respectively by the amount of each label present during the detection event. For a set of m detectors being used to detect n different labels during an experiment, a set of linear equations relating the observed m detector responses at the event with label abundances for each of the n labels at the event can be expressed as d=Ma, where d is an m×1 column vector of output measurements across all m detectors at the event, a is an n×1 column vector of label abundances of each of the n labels used in the experiment, and M is an m rowan column "spillover matrix." The spillover matrix M has entries $S_{ij}$, where $S_{ij}$ corresponds to the response of a detector i (where i runs from 1 to m) to a label j (where j runs from 1 to n). For example, the area of the "FITC spillover into PE" region of FIG. 2 is indicative of a spillover matrix entry where the detector i corresponds to the PE detector and the label j corresponds to the FITC label. When running an experiment, the detector outputs are measured for each event, and label abundances for each event are derived using the formula $a=M^{-1}d$, producing an abundance value for each label at each event based on the measured detector outputs at each event.

Methods for determining spectral overlap, generating a spillover matrix, generating compensation matrix, and performing compensation have been previously disclosed, for example, in U.S. Pat. Nos. 8,779,387, 8,004,674, 8,158,429, 8,158,429, 7,507,588, 4,704,891, 6,897,954, 8,865,470, 8,415,161, and 5,528,045, the content of each of which is incorporated herein by reference in its entirety. Additionally, methods for determining spectral overlap, generating a spillover matrix, generating compensation matrix, and performing compensation have been previously disclosed, for example, in U.S. Patent Application Publication 2018/0231452, published Aug. 16, 2018, and BD Biosciences Technical Bulletin: An Introduction to Compensation for Multicolor Assays on Digital Flow Cytometers (Published August 2009), the content of each of which is incorporated herein by reference in its entirety.

The signal captured at a fluorescent emission detector can comprise contributions from one or more fluorescent labels, a system background signal, and the autofluorescence noise signal. The system background, often referred to as "baseline," can be removed from a measured signal through a baseline restore process, wherein a baseline signal can be estimated from time intervals in a cytometry experiment in which no event is occurring and then subtracted from the measured signal. To compensate for autofluorescence, in conventional compensation techniques, a "negative" or unstained sample, and a "positive" sample, one containing cells stained with a single dye, can be measured for each fluorescent dye to be used in a cytometry experiment. A single global negative population can be defined from an unstained sample for each dye. The median fluorescence intensity (WI) of the single global negative population can be treated as the autofluorescence noise signal of the sample and can be subtracted from data of the positive sample to calculate an autofluorescence spillover value. In some embodiments, when a marker of interest expresses on more than one cell type in a sample, the conventional method may fail to accurately remove the autofluorescence noise signal because the autofluorescence noise signal of each cell type can vary in strength. Consequently, in some embodiments, autofluorescence can be mischaracterized as the fluorescence emission of one or more markers, even in the absence of such markers on a given cell type, which can make it difficult to distinguish populations not expressing a particular marker and those having a weak expression of that marker.

In some embodiments described herein, autofluorescence noise signal estimation can be adapted to cell scatter characteristics. Compensation methods have been previously disclosed, for example, in U.S. Pat. No. 10,145,793, the content of which is hereby expressly incorporated by reference in its entirety. Cells with a similar size and complexity are more likely to have similar autofluorescence. Because size and complexity of a particle can be correlated to the intensity measured by forward scatter detectors and side scatter detectors, respectively, estimating an autofluorescence noise signal for a small area of a forward scatter-side scatter plot can lead to a more accurate value than estimating the autofluorescence noise signal based on a single median fluorescence intensity. Forward scatter and side scatter intensity measurements can be used in conjunction with associated fluorescence intensity values to provide a plurality of estimated autofluorescence noise signals, each signal associated with an area of a forward scatter-side scatter plot. The estimated autofluorescence noise signal values can then be subtracted from the signals captured by the fluorescent emission detectors for a corresponding stained sample based at least in part on the areas of the forward scatter-side scatter plot associated with the autofluorescence noise signals so that the measured data will more directly correlate to markers and labels of interest.

There are provided, in some embodiments, systems, methods, compositions, and kits for performing compensation for multi-parameter flow cytometry. Disclosed herein include methods of utilizing bi-specific probes (e.g., bispecific reagents) that can enable any single-cell sample to be used as its own optimized single color compensation control samples.

There are provided, in some embodiments, binding moieties with dual recognition that can serve as a bridging agent for the preparation of cellular fluorescence control samples. The binding moieties disclosed herein (e.g., bispecific probes, bispecific reagents) can markedly improve spectral unmixing and/or compensation, and thus improve resolution, in multi-parameter flow cytometry.

In standard multi-parameter flow cytometry there is a need to address multiple fluorophore emissions spilling into detectors dedicated to other fluorophores (spectral overlap). This is commonly addressed using a computational method called compensation.

Rather than dedicating one detector to one fluorophore, new technologies are utilizing more of the spectral characteristics of each fluorophore using more detectors than dyes and spectrally unmixing signals from each fluorophore (spectral flow cytometry). This takes advantage of more of the fluorescence emission of each dye and can improve signal and resolution of different cell populations.

To address spectral overlap in either standard or spectral flow cytometry, single stained controls can be required to build a compensation matrix. To calculate an accurate compensation matrix, it can be advantageous for the single stained controls to be at least as bright as the stain in the multi-parameter panel. These single stained controls consist typically of either cells or particles (compensation beads) stained with only one of the fluorophores in the multiparameter panel. However, there are several drawbacks to either of these methods: (i) compensation beads intrinsically have different auto fluorescence than cells; (ii) polymer particles may impact the fluorescence characteristics of some dyes; (iii) different cell types intrinsically have different auto fluorescence from each other; (iv) some cell targets are very rarely expressed on the cells of interest, making it difficult to resolve positive and negative populations to build the compensation matrix; and/or (v) there are often differences in spectral characteristics from batch to batch of fluorophore conjugated antibodies (especially tandem fluorophores), so ideally one should use the same reagent sample for the single stained control as is used in the multi-parameter panel.

These potential drawbacks can be exacerbated in spectral flow cytometry, as any difference in spectral characteristics between the single stained controls and the multi-parameter panel are compounded since more of the spectra is collected for each fluorophore.

The methods and compositions provided herein can address the above-mentioned problems in the art. Disclosed herein include reagents which comprise two antibodies conjugated to one another to form a bispecific probe (e.g., bispecific reagent). One antibody (e.g., an anchor antibody, an anchor arm, an anchor probe) can have affinity for a highly expressed antigen on the surface of the cell of interest (such as, for example, anti-CD44 or anti-CD45 for human PBMCs), and the other antibody (e.g., capture antibody, a capture arm, a capture probe) can have affinity for each of the antibody-dye conjugates (e.g., detection reagents) in the multi-parameter panel (such as, for example, anti-mouse kappa light chain). For each fluorescently labeled antibody in the panel, the method can comprise staining a sample of the cells of interest with this bi-specific reagent, followed by one of the antibody-dye conjugates in the panel to serve as a single stain control.

The methods and compositions provided herein can reduce or eliminate any intrinsic differences in auto fluorescence between single stain control cells or beads and the cells of interest in the multi-parameter sample. Additionally, the disclosed methods and compositions can provide maximum and consistent signal for calculating the compensation matrix, and account for any potential variations from batch to batch of fluorophore conjugated antibodies. As described herein, the disclosed reagents can be conveniently generated using click chemistry (e.g., site directed chemistry), which can enable small, reproducible, batches to be built quickly and relatively cheaply, such that different combinations of anchor and capture antibodies can be utilized, making it useful for various cells of interest and different staining reagents in the multi-parameter panel.

The methods and compositions provided herein offer multiple advantages and improvements over currently available methods, such as, for example, (i) eliminating any difference in auto fluorescence between single stain controls and cells of interest; (ii) allowing for ample signal of any antibody-fluorophore conjugate, regardless of expression level on cells of interest; (iii) maintaining reagent fluorescence characteristics with biological model (vs. synthetic polymer control particles); and/or (iv) allowing use of the same antibody-fluorophore reagent for both single stain controls and multi-parameter panel to account for potential batch to batch variations in fluorophore spectral characteristics.

In some embodiments, the generation of the bi-specific reagents provided herein can comprise an anchor probe and a capture probe being conjugated together via click chemistry. The methods provided herein can enable quick and relatively inexpensive building of bi-specific reagents to stain different cell types of interest (such as, for example, mouse vs. human, primary immune cells vs. cell line). The methods and compositions provided herein can serve as an alternative to the use of compensation particles.

FIG. 3 depicts a non-limiting exemplary compensation workflow for multi-parameter flow cytometry. Single cell samples can be labeled with a unique bispecific (anchor/capture) probe. The bispecific probe (e.g., bispecific reagent) can comprise an anchor arm (e.g., anchor probe) and a capture arm (e.g., capture probe). This can be a rapid (e.g., 5 minute) antibody labeling step. Example anchor targets (e.g., cell surface targets bound by the capture arm of the bispecific probe) include ubiquitous immune system proteins, such as, for example, CD44 and/or CD45. Specific cell samples can then be individually labeled with fluorescently conjugated antibodies. The capture arm (e.g., capture probe) of the bispecific probe can be a generic antibody with high affinity to all antibodies with specific host species (e.g., anti-mouse kappa light chain). Cellular samples can now serve as brightly labeled single color fluorescence compensation particles. Single color control samples can be a gold standard in nearly all multi-parameter flow cytometry experiments.

The methods provided herein can serve as a replacement to compensation control sample tubes (such as compensation control beads stained with individual reagents to be used in the multicolor panel, or directly stained cells with reagent of interest or alternative antibodies conjugated to the same fluorophore) in a standard multicolor flow cytometry workflow. The samples can be run separately from, generally before, the experimental sample. The methods provided herein of generating accurate fluorescence controls are not limited to flow cytometry, but can also be utilized in any multifluorescence platform for analyzing cells or tissues (such as, for example, immunofluorescent imaging applications).

In some embodiments, the reagents provided herein comprise antibodies covalently bound to one another. In some embodiments, there are provided bispecific reagents comprising two antigen-binding moieties (e.g., an anchor probe and a capture probe). Each of the two antigen-binding moieties can be selected from a variety of affinity moieties. The affinity moieties can be associated (e.g., covalently attached) to each other by any means known in the art. In some embodiments, the method comprises the capture of fluorescently labeled antibodies at the surface of cells by a bispecific probe to serve as fluorescence control samples. Disclosed herein include reagents wherein covalent linking of full-size antibodies is employed generate a high performing bispecific. In some embodiments, there are provided single engineered (recombinant) antibodies with two different variable domains specific for different epitopes (e.g., a cell surface target and a detection reagent). In some embodiments, there are provided two monoclonal antibodies conjugated to one another.

In some embodiments, the method comprises adding the compensation control compositions provided herein to a fraction of the sample. In some embodiments, the anchor antibody (e.g., anchor probe) targets a relatively highly expressed antigen on the cells of interest. In some embodiments of the methods described herein, adequate compensation for standard or spectral flow requires the compensation controls to be as bright or brighter than the actual targeted stain in the multiplex panel. The target antibody can be recognized by the capture antibody (e.g., capture probe) of the bi-specific probes provided herein (for example, anti-mouse kappa will only bind to antibodies from a mouse host). The target antibody can be a user's reagent that is being employed in a multicolor experiment (which requires single color fluorescence control).

There are provided, in some embodiments, optimized fluorescence control samples which democratize multicolor flow cytometry and improve cell population resolution.

In standard multi-parameter flow cytometry, spill from multiple fluorophore emissions into detectors dedicated to other fluorophores (spectral overlap) is typically addressed using single stain controls via compensation. Significant spill can lead to increased spread of negative populations and reduced resolution of low expression targets of interest. Rather than dedicating one detector to one fluorophore, new technologies are utilizing more of the spectral characteristics of each fluorophore by using more detectors than dyes and spectrally unmixing signals from each fluorophore (spectral flow cytometry). This takes advantage of more of the fluorescence emission of each dye and can improve signal and resolution of different cell populations.

For either standard or spectral flow, to calculate an accurate compensation matrix it can be necessary for the single stain controls to be at least as bright as the stain in the multi-parameter panel. These single stained controls consist typically of either cells or particles (compensation beads) stained with only one of the fluorophores in the multi-parameter panel. However, there are several drawbacks to either of these methods, including but not limited to: (i) compensation beads intrinsically have different auto fluorescence than cells; (ii) polymer particles may impact the fluorescence characteristics of some dyes; (iii) different cell types intrinsically have different auto fluorescence from each other; (iv) some cell targets are very rarely expressed on the cells of interest, making it difficult to resolve positive and negative populations to build an accurate compensation matrix; and/or (v) there are often differences in spectral characteristics from batch to batch of fluorophore conjugated antibodies.

With less optimized panel design or higher parameter experiments, fluorescence spill can be quite significant. Due to inaccuracies in current compensation techniques, scientists often manually adjust the compensation matrix that is automatically generated by the software using single stained beads or cells. This requires flow cytometry expertise as well as biological understanding that isn't always known for a particular panel and sample. As scientists further elucidate disease states and search deeper for phenotypic biomarkers, the complexity of executing high parameter flow cytometry becomes the greatest obstacle to next generation precision diagnostics and therapy.

Disclosed herein include compositions and methods for generating optimized single-color stained controls from cells. The compensation methods and compositions provided herein were compared directly to standard bead-based compensation controls as well as single color stained samples. Utilizing standard auto-compensation algorithms alone, the resolution of key populations was dramatically improved, which simplifies the Flow Cytometry workflow and enables broader adoption of advanced multiparameter single cell analysis.

There are provided, in some embodiments, methods and compositions for determining spillover. In some embodiments, the method comprises: providing cells associated with a bispecific reagent and a first detection reagent, wherein the bispecific reagent comprises an anchor probe capable of specifically binding a cell surface target and a capture probe capable of specifically binding to the first detection reagent comprising a first label, wherein the emission spectrum of the first label comprises a first emission wavelength range and a first peak emission wavelength; providing an instrument comprising a first detector and a second detector, wherein the first detector is capable of detecting emissions within a first detection wavelength range and the second detector is capable of detecting emissions within a second detection wavelength range, wherein the first peak emission wavelength is within the first detection wavelength range and not within the second detection wavelength range, wherein a portion of the first emission wavelength range overlaps with the second detection wavelength range; and measuring, for one or more events of the cells associated with the bispecific reagent and the first detection reagent, emissions in the first detector to obtain a first reference value and emissions in the second detector to obtain a second reference value, wherein spillover comprises the second reference value. In some embodiments, the capture probe is capable of specifically binding to a second detection reagent, the method comprising: providing cells associated with the bispecific reagent and a second detection reagent comprising a second label; and measuring, for one or more events of the cells associated with the bispecific reagent and the second detection reagent, emissions in the first detector to obtain a third reference value and emissions in the second detector to obtain a fourth reference value.

There are provided, in some embodiments, methods and compositions for performing a multi-label experiment on an instrument comprising a first detector and a second detector. In some embodiments, the method comprises: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target, and wherein the second detection reagent is capable of specifically binding to the second cell target; providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; providing an instrument comprising a first detector and a second detector; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; measuring, for one or more events of the cells associated with the first detection reagent and the second detection reagent, emissions in the first detector to obtain a first experimental value and emissions in the second detector to obtain a second experimental value; and measuring, for one or more events of a plurality of unlabeled cells, emissions in the first detector to obtain a first background emission value and emissions in the second detector to obtain a second background emission value.

There are provided, in some embodiments, methods and compositions for performing compensation. In some embodiments, the method comprises: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target and the second detection reagent is capable of specifically binding to the second cell target; providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; providing an instrument comprising a first detector and a second detector; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; measuring, for one or more events of the cells associated with the first detection reagent and the second detection reagent, emissions in the first detector to obtain a first experimental value and emissions in the second detector to obtain a second experimental value; measuring, for one or more events of a plurality of unlabeled cells, emissions in the first detector to obtain a first background emission value and emissions in the second detector to obtain a second background emission value; and adjusting, for the one or more events of the cells associated with the first detection reagent and the second detection reagent, the first experimental value and/or the second experimental value based on one or more of the first, second, third, and fourth reference values and/or one or more of the first and second background emission values.

There are provided, in some embodiments, methods and compositions for generating a compensation matrix for an instrument for analyzing a plurality of labels using a plurality of detectors. In some embodiments, the method comprises: providing cells associated with a bispecific reagent and a first detection reagent and cells associated with a bispecific reagent and a second detection reagent, wherein the bispecific reagent comprises an anchor probe capable of specifically binding a cell surface target and a capture probe capable of specifically binding to the first detection reagent and the second detection reagent; measuring, for one or more events of the cells associated with the bispecific reagent and the first detection reagent, emissions in the first detector to obtain a first reference value and emissions in the second detector to obtain a second reference value; measuring, for one or more events of the cells associated with the bispecific reagent and the second detection reagent, emissions in the first detector to obtain a third reference value and emissions in the second detector to obtain a fourth reference value; and generating a compensation matrix based on one or more of the first, second, third, and fourth reference values.

There are provided, in some embodiments, methods and compositions for generating a compensation matrix. The method can comprise: generating a compensation matrix based on one or more of the first, second, third, and fourth reference values. The method can comprise: generating a compensation matrix based on one or more of the first, second, third, and fourth reference values and one or more of the first and second background emission values. Generating a compensation matrix based on one or more of the first, second, third, and fourth reference values can comprise: measuring, for one or more events of a plurality of unlabeled cells, emissions in the first detector to obtain a first background emission value and emissions in the second detector to obtain a second background emission value; and generating a compensation matrix based on one or more of the first, second, third, and fourth reference values and one or more of the first and second background emission values. Providing cells associated with a bispecific reagent and a first detection reagent can comprise: contacting a plurality of control cells comprising a cell surface target with the bispecific reagent to form cells associated with the bispecific reagent, wherein the bispecific reagent comprises an anchor probe capable of specifically binding to the cell surface target, and wherein the bispecific reagent comprises a capture probe capable of specifically binding to the first detection reagent and/or the second detection reagent; and contacting the first detection reagent with cells associated with the bispecific reagent to form cells associated with the bispecific reagent and the first detection reagent. Providing cells associated with a bispecific reagent and a second detection reagent can comprise: contacting a plurality of control cells comprising a cell surface target with the bispecific reagent to form cells associated with the bispecific reagent, wherein the bispecific reagent comprises an anchor probe capable of specifically binding to the cell surface target, and wherein the bispecific reagent comprises a capture probe capable of specifically binding to the first detection reagent and/or the second detection reagent; and contacting the second detection reagent with cells associated with the bispecific reagent to form cells associated with the bispecific reagent and the second detection reagent.

The method can comprise: measuring, for one or more events of a plurality of unlabeled cells, emissions in the first detector to obtain a first background emission value and emissions in the second detector to obtain a second background emission value. The method can comprise: contacting a first detection reagent comprising a first label and a second detection reagent comprising a second label with a plurality of sample cells comprising a first cell target and a second cell target to form cells associated with the first detection reagent and the second detection reagent, wherein the first detection reagent is capable of specifically binding to the first cell target, and wherein the second detection reagent is capable of specifically binding to the second cell target; and measuring, for one or more events of the cells associated with the first detection reagent and the second detection reagent, emissions in the first detector to obtain a first experimental value and emissions in the second detector to obtain a second experimental value. The method can comprise: adjusting, for the one or more events of the cells associated with the first detection reagent and the second detection reagent, the first experimental value and/or the second experimental value based on one or more of the first, second, third, and fourth reference values and/or one or more of the first and second background emission values. The method can comprise: adjusting, for the one or more events of the cells associated with the first detection reagent and the second detection reagent, the first experimental value and/or the second experimental value based on a spillover matrix and/or a compensation matrix.

There are provided, in some embodiments, methods and compositions for generating a spillover matrix. In some embodiments, generating a compensation matrix based on one or more of the first, second, third, and fourth reference values can comprise: generating a spillover matrix based on one or more of the first, second, third, and fourth reference values. The method can comprise: generating a spillover matrix based on one or more of the first, second, third, and fourth reference values. The method can comprise: generating a spillover matrix based on one or more of the first, second, third, and fourth reference values and/or one or more of the first and second background emission values. The method can comprise: generating a compensation matrix based on a spillover matrix. The compensation matrix can be the inverse of the spillover matrix. The compensation matrix can be stored in the instrument for subsequent use. Spillover can comprise emissions of the first label detected by the second detector and/or emissions of the second label detected by the first detector.

The plurality of control cells, the plurality of unlabeled cells, and/or the plurality of sample cells can be derived from the same cell sample. The plurality of control cells, the plurality of unlabeled cells, and/or the plurality of sample cells can comprise a plurality of single cells. The plurality of control cells, the plurality of unlabeled cells, and/or the plurality of sample cells can comprise a heterogeneous cell population. The plurality of control cells, the plurality of unlabeled cells, and/or the plurality of sample cells can comprise two or more cell types. The number of cell types within a cell sample can be, can be about, can be at least, or can be at most, 1, 2, 3, 4, 5, 6, 7, 8, 9, 10, 20, 30, 40, 50, 60, 70, 80, 90, 100, or a number or a range between any of these values, of cell types. The one or more events can comprise about 10 events to about 100,000 events. In some embodiments, the number of events can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of events can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. The plurality of unlabeled cells can be not associated with a first detection reagent or a second detection reagent. The plurality of unlabeled cells can be not associated with a label. The plurality of unlabeled cells can be not associated with a fluorophore.

The emissions in the first detector of the one or more events of the cells associated with the bispecific reagent and the first detection reagent can be as high as the emissions in the first detector of the one or events of the cells associated with the first detection reagent and the second detection reagent. The emissions in the first detector of the one or more events of the cells associated with the bispecific reagent and the first detection reagent can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, higher than the emissions in the first detector of the one or more events of the cells associated with the first detection reagent and the second detection reagent. The emissions in the second detector of the one or more events of the cells associated with the bispecific reagent and the second detection reagent can be as high as the emissions in the second detector of the one or more events of the cells associated with the first detection reagent and the second detection reagent. The emissions in the second detector of the one or more events of the cells associated with the bispecific reagent and the second detection reagent can be, or can be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900%, 1000%, or a number or a range between any two of these values, higher than the emissions in the second detector of the one or more events of the cells associated with the first detection reagent and the second detection reagent.

The methods and compositions provided herein can be employed with a variety of instruments. The instrument can comprise a flow cytometer. The flow cytometer can comprise a conventional flow cytometer. The flow cytometer can comprise spectral flow cytometer, a hyperspectral flow cytometer, an imaging flow cytometer, or any combination thereof. The instrument can comprise a multi-fluorescence imaging system. The instrument can comprise a fluorescence microscope. The instrument can comprise a protein array. The measuring can comprise performing an immunohistochemistry assay. The measuring can comprise performing an enzyme-linked immunosorbent assay (ELISA). The first detector and/or second detector can be paired with one or more filters. The one or more filters can comprise a long pass filter, a short pass filter, a band pass filter, or any combination thereof. The instrument can comprise one or more excitation lasers. The first detector and/or second detector can comprise photodetectors. The first detector and/or second detector can comprise fluorescence emission detectors. The first label and/or the second label can comprise a fluorophore.

The emissions can comprise fluorescence emissions. One or more of the first, second, third, and fourth reference values, one or more of the first and second background emission values, and/or one or more of the first and second experimental values can comprise a fluorescence intensity value. One or more of the first, second, third, and fourth reference values, one or more of the first and second background emission values, and/or one or more of the first and second experimental values can comprise a mean fluorescence intensity value. One or more of the first, second, third, and fourth reference values, one or more of the first and second background emission values, and/or one or more of the first and second experimental values can comprise a median fluorescence intensity value. The first background emission value and/or the second background emission value can comprise autofluorescence. The first detection reagent can comprise a third label. The first label and third label can be capable of fluorescence resonance energy transfer (FRET) when brought in close proximity. The first label and the third label can comprise tandem dyes (e.g., PE-Cy™7, APC-Cy™7).

The emission spectrum of the first label can comprise a first emission wavelength range and a first peak emission wavelength. The emission spectrum of the second label can comprise a second emission wavelength range and a second peak emission wavelength. The first detector can be capable of detecting emissions within a first detection wavelength range. The second detector can be capable of detecting emissions within a second detection wavelength range. The second emission wavelength range can be different from the first detection wavelength range. The second peak emission wavelength can be different from the first peak emission wavelength. The first emission wavelength range can be different from the second detection wavelength range. The first peak emission wavelength range can be different from the second peak emission wavelength range. In some embodiments, a portion of the first emission wavelength range overlaps with the second detection wavelength range. In some embodiments, a portion of the second emission wavelength range overlaps with the first detection wavelength range. The first peak emission wavelength can be within the first detection wavelength range, and the first peak emission wavelength can be not within the second detection wavelength range. The second peak emission wavelength can be within the second detection wavelength range, and the second peak emission wavelength can be not within the first detection wavelength range. The first detector can be the primary detector of the first label and the second detector can be the secondary detector of the first label. The second detector can be the primary detector of the second label and the first detector can be the secondary detector of the second label. In some embodiments, the percentage of the second emission wavelength range that overlaps with the first detection wavelength range and/or the percentage of the first emission wavelength range that overlaps with the second detection wavelength range can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or a number or a range between any two of these values. In some embodiments, the percentage of the second emission wavelength range that overlaps with the first detection wavelength range and/or the percentage of the first emission wavelength range that overlaps with the second detection wavelength range can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.99%.

The instrument can comprise a forward scatter detector and a side scatter detector. The method can comprise: measuring, for one or more events of the unlabeled cells, for one or more events of the cells associated with the bispecific reagent and the first detection reagent and/or for one or more events of the cells associated with the bispecific reagent and the second detection reagent, a forward scatter value and a side scatter value. The method can comprise: determining forward scatter-side scatter plot locations of one or more events of the unlabeled cells, of one or more events of the cells associated with the bispecific reagent and the first detection reagent, and/or of one or more events of the cells associated with the bispecific reagent and the second detection reagent based on the forward scatter value and the side scatter value. The method can comprise: associating the forward scatter-side scatter plot locations of one or more events of the unlabeled cells, of one or more events of the cells associated with the bispecific reagent and the first detection reagent, and/or of one or more events of the cells associated with the bispecific reagent and the second detection reagent with forward scatter-side scatter plot regions. In some embodiments, a forward scatter-side scatter plot region can comprise a plurality of adjacent forward scatter-side scatter plot locations. In some embodiments, a forward scatter-side scatter plot region can comprise the forward scatter-side scatter plot locations of about 10 events to about 100,000 events. In some embodiments, a forward scatter-side scatter plot region comprises the forward scatter-side scatter plot locations of about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values, events. The events of cells of the same cell type can be associated with the same forward scatter-side scatter plot region. The events of cells of the different cell types can be associated with the different forward scatter-side scatter plot regions. The two or more cell types can be associated with different forward scatter-side scatter plot regions. The method can comprise: associating the first reference value and/or the second reference value of one or more events of the cells associated with the bispecific reagent and the first detection reagent with one or more forward scatter-side scatter plot regions. The method can comprise: associating the third reference value and/or the fourth reference value of one or more events of the cells associated with the bispecific reagent and the second detection reagent with one or more forward scatter-side scatter plot regions. The method can comprise: associating the first background emission value and/or the second background emission value of one or more events of the unlabeled cells with one or more forward scatter-side scatter plot regions. The method can comprise: generating a spillover matrix and/or a compensation matrix for one or more forward scatter-side scatter plot regions based on one or more of the first, second, third, and fourth reference values and/or one or more of the first and second background emission values associated with the respective forward scatter-side scatter plot regions. The method can comprise: measuring, for one or more events of the cells associated with the first detection reagent and the second detection reagent, a forward scatter value and a side scatter value. The method can comprise: determining the forward scatter-side scatter plot locations of one or more events of the cells associated with the first detection reagent and the second detection reagent based on the forward scatter value and the side scatter value. The method can comprise: associating the forward scatter-side scatter plot locations of one or more events of the cells associated with the first detection reagent and the second detection reagent with forward scatter-side scatter plot regions. The method can comprise: adjusting, for the one or more events of the cells associated with the first detection reagent and the second detection reagent, the first experimental value and/or the second experimental value based on the one or more of the first, second, third, and fourth reference values and/or one or more of the first and second background emission values associated with the respective forward scatter-side scatter plot regions. The method can comprise: adjusting, for the one or more events of the cells associated with the first detection reagent and the second detection reagent, the first experimental value and/or the second experimental value based on the spillover matrix and/or compensation matrix associated with the respective forward scatter-side scatter plot region.

In some embodiments, the use of the bispecific reagent increases resolution sensitivity by at least about five percent as compared to a comparable method that does not employ the bispecific reagent, wherein resolution sensitivity comprises the ability of the instrument to differentiate between dimly labeled cells and unlabeled cells. The dimly labeled cells can comprise cells associated with the first detection reagent and the second detection reagent for which the first experimental value is less than about 50% (e.g., 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values) greater than the first background emission value. The dimly labeled cells can comprise cells associated with the first detection reagent and the second detection reagent for which the second experimental value is less than about 50% (e.g., 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values) greater than the second background emission value. In some embodiments, the comparable method employs compensation beads (e.g., BD CompBeads, One-Comp beads, UltraComp beads, VersaComp beads, or any combination thereof). In some embodiments, the comparable method employs compensation beads to generate a spillover matrix and/or a compensation matrix.

In some embodiments, the method comprises determining one or more characteristics of the sample cells based on the first experimental value and/or the second experimental value of the cells associated with one or more events of the cells associated with the first detection reagent and the second detection reagent. The more of more characteristics can comprise the number of copies of the first cell target and/or the second cell target in one or more of the plurality of sample cells. The first cell target and/or second cell target can comprise a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. The first cell target and/or second cell target can be on a cell surface.

The bispecific reagent can comprise a plurality of bispecific reagents. The plurality of bispecific reagents can comprise identical bispecific reagents. The plurality of bispecific reagents can comprise a mixture of two or more distinct bispecific reagents. The bispecific reagent can comprise a bispecific reagent composition comprising a mixture of two or more distinct bispecific reagents. The two or more distinct bispecific reagents can be capable of specifically binding to distinct detection reagents. The two or more distinct bispecific reagents can be capable of specifically binding to distinct cell surface targets. The method can comprise: after contacting the plurality of bispecific reagents with the plurality of control cells, removing one or more bispecific reagents of the plurality of bispecific reagents that are not contacted with the plurality of control cells. Removing the one or more bispecific reagents not contacted with the plurality of control cells can comprise: removing the one or more bispecific reagents not contacted with the cell surface target.

The first detection reagent can comprise a plurality of the first detection reagents. The second detection reagent can comprise a plurality of the second detection reagents. The method can comprise: after contacting the plurality of first detection reagents and the plurality of second detection reagents with a plurality of sample cells, removing one or more first detection reagents and one or more second detection reagents of the plurality of first detection reagents and plurality of second detection reagents that are not contacted with the plurality of sample cells. Removing one or more first detection reagents and one or more second detection reagents of the plurality of first detection reagents and plurality of second detection reagents that are not contacted with the plurality of sample cells can comprise: removing the one or more first detection reagents and the one or more second detection reagents not contacted with the first cell target and the second cell target, respectively. The method can comprise: after contacting the plurality of first detection reagents with the cells associated with the bispecific reagent, removing one or more first detection reagents of the plurality of first detection reagents that are not contacted with the cells associated with the bispecific reagent. Removing one or more first detection reagents of the plurality of first detection reagents that are not contacted with the cells associated with the bispecific reagent can comprise: removing the one or more first detection reagents not contacted with the bispecific reagent. The method can comprise: after contacting the plurality of second detection reagents with the cells associated with the bispecific reagent, removing one or more second detection reagents of the plurality of second detection reagents that are not contacted with the cells associated with the bispecific reagent. Removing one or more second detection reagents of the plurality of second detection reagents that are not contacted with the cells associated with the bispecific reagent can comprise: removing the one or more second detection reagents not contacted with the bispecific reagent.

Bispecific Reagents

There are provided, in some embodiments, bispecific reagents comprising one, two, or more, antigen-binding moieties. The capture probe can comprise an antigen binding moiety configured to bind a detection reagent (e.g., a first detection reagent, a second detection reagent) as described herein. The anchor probe can comprise an antigen binding moiety configured to bind a cell surface target as described herein. The detection reagent can comprise an antigen binding moiety configured to bind a cell target (e.g., a first cell target, a second cell target) as described herein. Antigen-binding moieties can comprise antibodies, antibody fragments, and variants. In some embodiments, antibody fragments and variants can comprise antigen binding regions from intact antibodies. Examples of antibody fragments and variants can include, but are not limited to Fab, Fab', F(ab')2, and Fv fragments; diabodies; linear antibodies; single-chain antibody molecules such as single chain variable fragment (scFv); and multi specific antibodies formed from antibody fragments.

For the purposes herein, the term "antibody" shall be given its ordinary meaning and can also comprise a heavy and light variable domain as well as an Fc region. As used herein, the term "native antibody" can refer to a heterotetrameric glycoprotein of about 150,000 Daltons, composed of two identical light (L) chains and two identical heavy (H) chains. Each light chain can be linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VT) followed by a number of constant domains. Each light chain has a variable domain at one end (VL) and a constant domain at its other end: the constant domain of the light chain is aligned with the first constant domain of the heavy chain, and the light chain variable domain is aligned with the variable domain of the heavy chain.

As used herein, the term "variable domain" can refer to specific antibody domains found on both the antibody heavy and light chains that differ extensively in sequence among antibodies and are used in the binding and specificity of each particular antibody for its particular antigen. Variable domains can comprise hypervariable regions. As used herein, the term "hypervariable region" can refer to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" can refer to a region of an antibody comprising a structure that is complimentary to its target antigen or epitope. Other portions of the variable domain, not interacting with the antigen, are referred to as framework (FVV) regions. The antigen-binding site (also known as the antigen combining site or paratope) comprises the amino acid residues necessary to interact with a particular antigen. The exact residues making up the antigen-binding site are typically elucidated by co-crystallography with bound antigen, however computational assessments based on comparisons with other antibodies can also be used. Determining residues that make up CDRs may include the use of numbering schemes including, but not limited to, those taught by Kabai, Chothia, and Honegger.

H and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs has favored canonical structures with the exception of the CDR-H3, which comprises amino acid sequences that may be highly variable in sequence and length between antibodies resulting in a variety of three-dimensional structures in antigen-binding domains. In some cases, CDR-H3s may be analyzed among a panel of related antibodies to assess antibody diversity. Various methods of determining CDR sequences are known in the art and may be applied to known antibody sequences.

As used herein, the term "Fv" can refer to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage but are largely unstable. Recombinant methods are known in the art for generating stable Fv fragments, typically through insertion of a flexible linker between the light chain variable domain and the heavy chain variable domain (to form a single chain Fv (scFv)) or through the introduction of a disulfide bridge between heavy and light chain variable domains.

As used herein, the term "light chain" can refer to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "single chain Fv" or "scFv" can refer to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. Using molecular genetics, two scFvs can be engineered in tandem into a single polypeptide, separated by a linker domain, called a "tandem scFv" (tascFv). Construction of a tascFv with genes for two different scFvs yields a "bispecific single-chain variable fragments" (bis-scFvs).

As used herein, the term "bispecific antibody" can refer to an antibody capable of binding two different antigens. Such antibodies typically comprise regions from at least two different antibodies. As used herein, the term "diabody" can refer to a small antibody fragment with two antigen-binding sites. Diabodies are functional bispecific single-chain antibodies (bscAb). Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites.

As used herein, the term "monoclonal antibody" can refer to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" can indicate the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "antibody variant" can refer to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG 1, IgG2, IgG3, IgG4, or IgM), humanized variants, optimized variants, multi-specific antibody variants (e.g., bispecific variants), and antibody fragments.

In some embodiments, the antigen-binding moieties provided herein comprise antibody mimetics (e.g., monobodies). As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (e.g., the protein scaffolds disclosed in U.S. Pat. Nos. 6,673,901 and 6,348,584). In some embodiments, antibody mimetics may be those known in the art including, but are not limited to affibody molecules, affitins, anticalins, avimers, Centyrins, DARPINSTM, Fynomers and Kunitz and domain peptides. In other embodiments, antibody mimetics may include one or more non-peptide regions.

In some embodiments, the antigen-binding moieties provided herein comprise multispecific antibodies that bind more than one epitope. As used herein, the terms "multibody" or "multispecific antibody" can refer to an antibody wherein two or more variable regions bind to different epitopes. The epitopes may be on the same or different targets. In some embodiments, a multi-specific antibody is a "bispecific antibody" which recognizes two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

There are provided, in some embodiments, bispecific reagents. One or more of the first detection reagent, the second detection reagent, the bispecific reagent, the capture probe, and the anchor probe can comprise an antibody or fragment thereof. The capture probe can be capable of specifically binding to a light chain constant domain and/or a heavy chain constant domain. The first detection reagent and/or the second detection reagent can comprise a heavy chain constant domain and/or a light chain constant domain. The heavy chain constant domain can comprise the constant domains of IgG1, IgG2, IgG3, IgG4, IgM, IgA1, IgA2, IgD, IgE, or any combination thereof. The light chain constant domain can be a lambda light chain constant domain and/or a kappa light chain constant domain. The antibody or fragment thereof can be derived from a mouse, rat, guinea pig, hamster, rabbit, cat, dog, monkey, cow, pig, horse, goat, sheep, or any combination thereof. The antibody or fragment thereof can comprise a Fab, a Fab', a F(ab)$_2$, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

The bispecific reagent can comprise a conjugate of an antibody or fragment thereof and an antibody or fragment thereof. The antibody or fragment thereof can comprise a monoclonal antibody. The antibody or fragment thereof can be conjugated to the antibody or fragment thereof via chemical coupling, genetic fusion, noncovalent association, or any combination thereof. The conjugate can be formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. The conjugate can be formed by a reaction between acetylene and azide. The conjugate can be formed by a reaction between an aldehyde or ketone group and a hydrazine or alkoxy amine.

The cell surface target can comprise a carbohydrate, a lipid, a protein, or any combination thereof. The cell surface target can comprise CD1a, CD1b, CD1c, CD1d, CD1e, CD2, CD3, CD3d, CD3e, CD3g, CD4, CD5, CD6, CD7, CD8a, CD8b, CD9, CD10, CD11a, CD11b, CD11c, CD11d, CDw12, CD13, CD14, CD15, CD15u, CD15s, CD15su, CD16, CD16b, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD45, CD45RA, CD45RB, CD45RC, CD45RO, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CD75, CD75s, CD77, CD79a, CD79b, CD80, CD81, CD82, CD83, CD84, CD85s, CD85d, CD85j, CD85k, CD86, CD87, CD88, CD89, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140a, CD140b, CD141, CD142, CD143, CD144, CDw145, CD146, CD147, CD148, CDw149, CD150, CD151, CD152, CD153, CD154, CD155, CD156a, CD156b, CD156c, CD157, CD158e, CD158i, CD158k, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD194, CD195, CD196, CD197, CDw198, CD199, CD200, CD201, CD202b, CD203c, CD204, CD205, CD206, CD207, CD208, CD209, CD210, CDw210b, CD212, CD213a1, CD213a2, CD215, CD217a, CD218a, CD218b, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240DCE, CD240D, CD241, CD242, CD243, CD244, CD245, CD246, CD247, CD248, CD249, CD252, CD253, CD254, CD256, CD266, CD267, CD268, CD269, CD270, CD271, CD272, CD273, CD274, CD275, CD276, CD277, CD278, CD279, CD280, CD281, CD282, CD283, CD284, CD286, CD289, CD290, CD292, CDw293, CD294, CD295, CD296, CD297, CD298, CD299, CD300a, CD300c, CD300e, CD301, CD302, CD303, CD304, CD305, CD306, CD307a, CD307b, CD307c, CD307d, CD307e, CD308, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362, CD363, CD364, CD365, CD366, CD367, CD368, CD369, CD370, CD371, BCMA, a HLA protein, (32-microglobulin, or any combination thereof. The cell surface target can be at least about 2-fold (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) more abundant than the first cell target and/or the second cell target.

Compositions and Kits

There are provided, in some embodiments, kits and compositions. In some embodiments, the composition (e.g., kit) comprises: a cell associated with a bispecific reagent, wherein the bispecific reagent comprises an anchor probe specifically bound to a cell surface target on the cell and a capture probe capable of specifically binding to a detection reagent. The detection reagent can be capable of specifically binding to a cell target. The cell surface target can be at least about 2-fold (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) more abundant than the cell target. One or more of the bispecific reagent, the detection reagent, the capture probe, and/or the anchor probe can comprise an antibody or fragment thereof. The capture probe can be capable of specifically binding to a light chain constant domain and/or a heavy chain constant domain. The detection reagent can comprise a heavy chain constant domain and/or a light chain constant domain. The detection reagent can comprise a fluorophore. The heavy chain constant domain can comprise the constant domains of IgG1, IgG2, IgG3, IgG4, IgM, IgA1, IgA2, IgD, IgE, or any combination thereof. The light chain constant domain can comprise a lambda light chain constant domain and/or a kappa light chain constant domain. The bispecific reagent can comprise a conjugate of an antibody or fragment thereof and an antibody or fragment thereof. The antibody or fragment thereof can be conjugated to the antibody or fragment thereof via chemical coupling, genetic fusion, noncovalent association, or any combination thereof. The conjugate can be formed by a 1,3-dipolar cycloaddition reaction, a hetero-Diels-Alder reaction, a nucleophilic substitution reaction, a non-aldol type carbonyl reaction, an addition to carbon-carbon multiple bond, an oxidation reaction, a click reaction, or any combination thereof. The conjugate can be formed by a reaction between acetylene and azide. The conjugate can be formed by a reaction between an aldehyde or ketone group and a hydrazine or alkoxy amine. The antibody or fragment thereof can comprise a monoclonal antibody, a Fab, a Fab', a F(ab')2, a Fv, a scFv, a dsFv, a diabody, a triabody, a tetrabody, a multispecific antibody formed from antibody fragments, a single-domain antibody (sdAb), a single chain comprising complementary scFvs (tandem scFvs) or bispecific tandem scFvs, an Fv construct, a disulfide-linked Fv, a dual variable domain immunoglobulin (DVD-Ig) binding protein or a nanobody, an aptamer, an affibody, an affilin, an affitin, an affimer, an alphabody, an anticalin, an avimer, a DARPin, a Fynomer, a Kunitz domain peptide, a monobody, or any combination thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for performing compensation, the method comprising:
    contacting a first detection reagent comprising a first label and a second detection reagent comprising a second label with a plurality of sample cells comprising a first cell target and a second cell target to form cells associated with the first detection reagent and the second detection reagent, wherein the first detection reagent comprises an antibody or fragment thereof capable of specifically binding to the first cell target, and the second detection reagent comprises an antibody or fragment thereof capable of specifically binding to the second cell target;
    providing cells associated with a bispecific reagent and a first detection reagent and cells associated with a bispecific reagent and a second detection reagent, wherein the bispecific reagent comprises an anchor probe and a capture probe, wherein the anchor probe comprises an antibody or fragment thereof capable of specifically binding a cell surface target and the capture probe comprises an antibody or fragment thereof which has affinity to an antibody or fragment thereof derived from a host species, and wherein the first detection reagent and the second detection reagent are derived from said host species;
    providing an instrument comprising a first detector and a second detector;
    measuring, for one or more events of the cells associated with the bispecific reagent and the first detection reagent, emissions in the first detector to obtain a first reference value and emissions in the second detector to obtain a second reference value;
    measuring, for one or more events of the cells associated with the bispecific reagent and the second detection reagent, emissions in the first detector to obtain a third reference value and emissions in the second detector to obtain a fourth reference value;
    measuring, for one or more events of the cells associated with the first detection reagent and the second detection reagent, emissions in the first detector to obtain a first experimental value and emissions in the second detector to obtain a second experimental value;
    measuring, for one or more events of a plurality of unlabeled cells, emissions in the first detector to obtain a first background emission value and emissions in the second detector to obtain a second background emission value; and
    adjusting, for the one or more events of the cells associated with the first detection reagent and the second detection reagent, the first experimental value and/or the second experimental value based on one or more of the first, second, third, and fourth reference values and/or one or more of the first and second background emission values.

2. The method of claim 1, comprising generating a compensation matrix based on one or more of the first, second, third, and fourth reference values and one or more of the first and second background emission values.

3. The method of claim 1,
wherein providing cells associated with a bispecific reagent and a first detection reagent comprises:
contacting a plurality of control cells comprising a cell surface target with the bispecific reagent to form cells associated with the bispecific reagent; and
contacting the first detection reagent with cells associated with the bispecific reagent to form cells associated with the bispecific reagent and the first detection reagent; and
wherein providing cells associated with a bispecific reagent and a second detection reagent comprises:
contacting a plurality of control cells comprising a cell surface target with the bispecific reagent to form cells associated with the bispecific reagent; and
contacting the second detection reagent with cells associated with the bispecific reagent to form cells associated with the bispecific reagent and the second detection reagent.

4. The method of claim 1, comprising generating a spillover matrix based on: (i) one or more of the first, second, third, and fourth reference values; and/or (ii) one or more of the first, second, third, and fourth reference values and/or one or more of the first and second background emission values.

5. The method of claim 1, wherein the plurality of control cells, the plurality of unlabeled cells, and/or the plurality of sample cells: (i) are derived from the same cell sample; (ii) comprise a plurality of single cells; (iii) comprise a heterogeneous cell population; and/or (iv) comprise two or more cell types.

6. The method of claim 1, wherein the plurality of unlabeled cells are not associated with: (i) a first detection reagent or a second detection reagent; (ii) a label; and/or (iii) a fluorophore.

7. The method of claim 1, wherein the instrument comprises a flow cytometer, a fluorescence microscope, a protein array, one or more excitation lasers, a multi-fluorescence imaging system, or any combination thereof, and wherein the first detector and/or second detector comprise photodetectors and/or fluorescence emission detectors.

8. The method of claim 1, wherein: (i) the first label and/or the second label comprise a fluorophore; (ii) the emissions comprise fluorescence emissions; and/or (iii) the first background emission value and/or the second background emission value comprise autofluorescence.

9. The method of claim 1, wherein:
(i) the emission spectrum of the first label comprises a first emission wavelength range and a first peak emission wavelength;
(ii) the emission spectrum of the second label comprises a second emission wavelength range and a second peak emission wavelength;
(iii) the first detector is capable of detecting emissions within a first detection wavelength range;
(iv) the second detector is capable of detecting emissions within a second detection wavelength range, wherein the second emission wavelength range is different from the first detection wavelength range;
(v) the second peak emission wavelength is different from the first peak emission wavelength;
(vi) the first emission wavelength range is different from the second detection wavelength range;
(vii) the first peak emission wavelength range is different from the second peak emission wavelength range;
(viii) a portion of the first emission wavelength range overlaps with the second detection wavelength range;
(ix) a portion of the second emission wavelength range overlaps with the first detection wavelength range;
(x) the first peak emission wavelength is within the first detection wavelength range, and wherein the first peak emission wavelength is not within the second detection wavelength range; and/or
(xi) the second peak emission wavelength is within the second detection wavelength range, and wherein the second peak emission wavelength is not within the first detection wavelength range.

10. The method of claim 1, comprising:
measuring, for one or more events of the unlabeled cells, for one or more events of the cells associated with the bispecific reagent and the first detection reagent and/or for one or more events of the cells associated with the bispecific reagent and the second detection reagent, a forward scatter value and a side scatter value; and
determining forward scatter-side scatter plot locations of one or more events of the unlabeled cells, of one or more events of the cells associated with the bispecific reagent and the first detection reagent, and/or of one or more events of the cells associated with the bispecific reagent and the second detection reagent based on the forward scatter value and the side scatter value.

11. The method of claim 10, comprising associating the forward scatter-side scatter plot locations of one or more events of the unlabeled cells, of one or more events of the cells associated with the bispecific reagent and the first detection reagent, and/or of one or more events of the cells associated with the bispecific reagent and the second detection reagent with forward scatter-side scatter plot regions.

12. The method of claim 11, wherein a forward scatter-side scatter plot region comprises a plurality of adjacent forward scatter-side scatter plot locations, and wherein a forward scatter-side scatter plot region comprises the forward scatter-side scatter plot locations of about 10 events to about 100,000 events.

13. The method of claim 11, wherein the events of cells of the same cell type are associated with the same forward scatter-side scatter plot region, and wherein the events of cells of the different cell types are associated with the different forward scatter-side scatter plot regions.

14. The method of claim 11, comprising:
(i) associating the first reference value and/or the second reference value of one or more events of the cells associated with the bispecific reagent and the first detection reagent with one or more forward scatter-side scatter plot regions;
(ii) associating the third reference value and/or the fourth reference value of one or more events of the cells associated with the bispecific reagent and the second detection reagent with one or more forward scatter-side scatter plot regions; and/or
(iii) associating the first background emission value and/or the second background emission value of one or more events of the unlabeled cells with one or more forward scatter-side scatter plot regions.

15. The method of claim 11, comprising:
measuring, for one or more events of the cells associated with the first detection reagent and the second detection reagent, a forward scatter value and a side scatter value; and
determining the forward scatter-side scatter plot locations of one or more events of the cells associated with the first detection reagent and the second detection reagent based on the forward scatter value and the side scatter value.

16. The method of claim 15, comprising associating the forward scatter-side scatter plot locations of one or more events of the cells associated with the first detection reagent and the second detection reagent with forward scatter-side scatter plot regions.

17. The method of claim 16, comprising adjusting, for the one or more events of the cells associated with the first detection reagent and the second detection reagent, the first experimental value and/or the second experimental value based on the one or more of the first, second, third, and fourth reference values and/or one or more of the first and second background emission values associated with the respective forward scatter-side scatter plot regions.

18. The method of claim 16, comprising:
generating a spillover matrix and/or a compensation matrix for one or more forward scatter-side scatter plot regions based on one or more of the first, second, third, and fourth reference values and/or one or more of the first and second background emission values associated with the respective forward scatter-side scatter plot regions; and
adjusting, for the one or more events of the cells associated with the first detection reagent and the second detection reagent, the first experimental value and/or the second experimental value based on the spillover matrix and/or compensation matrix associated with the respective forward scatter-side scatter plot region.

19. The method of claim 1, wherein the use of the bispecific reagent increases resolution sensitivity by at least about 5% as compared to a comparable method that does not employ the bispecific reagent, and wherein resolution sensitivity comprises the ability of the instrument to differentiate between dimly labeled cells and unlabeled cells.

20. The method of claim 19, wherein dimly labeled cells comprise cells associated with the first detection reagent and the second detection reagent for which: (i) the first experimental value is less than about 50%, about 40%, about 30%, about 20%, about 10%, or about 5%, greater than the first background emission value; and/or (ii) the second experimental value is less than about 50%, about 40%, about 30%, about 20%, about 10%, or about 5%, greater than the second background emission value.

21. The method of claim 19, wherein the comparable method employs compensation beads to generate a spillover matrix and/or a compensation matrix.

22. The method of claim 1, comprising determining one or more characteristics of the sample cells based on the first experimental value and/or the second experimental value of one or more events of the cells associated with the first detection reagent and the second detection reagent.

23. The method of claim 1, wherein the cell surface target comprises CD339.

* * * * *